United States Patent [19]
Foulon et al.

[11] Patent Number: 6,090,818
[45] Date of Patent: Jul. 18, 2000

[54] INDOLIN-2-ONE DERIVATIVES, METHOD FOR PREPARING THEM AND PHARMACEUTICAL COMPOSITIONS CONTAINING THEM

[75] Inventors: Loïc Foulon, Garonne; Claudine Serradeil-Le Gal, Escalquens; Gérard Valette, Lacroix-Falguarde, all of France

[73] Assignee: Sanofi-Synthelabo, Paris, France

[21] Appl. No.: 09/331,007
[22] PCT Filed: Dec. 11, 1997
[86] PCT No.: PCT/FR97/02270
  § 371 Date: Jun. 14, 1999
  § 102(e) Date: Jun. 14, 1999
[87] PCT Pub. No.: WO98/25901
  PCT Pub. Date: Jun. 18, 1998

[30] Foreign Application Priority Data

Dec. 13, 1996 [FR] France ................................. 96 15384

[51] Int. Cl.[7] ..................... C07D 213/04; C07D 209/10; A61K 31/395; A61K 31/404
[52] U.S. Cl. ........................ 514/278; 514/418; 546/15; 548/411; 544/70
[58] Field of Search ............... 546/15; 548/411; 514/278, 418; 544/70

[56] References Cited

U.S. PATENT DOCUMENTS

| | | | |
|---|---|---|---|
| 4,226,860 | 10/1980 | Demerson et al. | 424/240 |
| 4,395,416 | 7/1983 | Langlois et al. | 424/267 |
| 5,618,833 | 4/1997 | Foulon et al. | 514/409 |
| 5,663,431 | 9/1997 | DiMalta et al. | 562/828 |
| 5,776,969 | 7/1998 | James | 514/418 |

*Primary Examiner*—Johann Richter
*Assistant Examiner*—Sonya N. Wright
*Attorney, Agent, or Firm*—Michael D. Alexander

[57] ABSTRACT

The invention relates to compounds with formula (I), a process for their preparation and pharmaceutical compositions containing them. These compounds have an excellent affinity for vasopressin and/or oxytocin

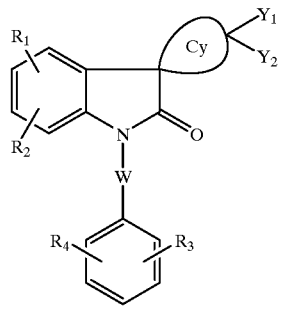

(I)

18 Claims, No Drawings

INDOLIN-2-ONE DERIVATIVES, METHOD FOR PREPARING THEM AND PHARMACEUTICAL COMPOSITIONS CONTAINING THEM

CROSS REFERENCE TO RELATED APPLICATIONS

This application is a filing under 35 U.S.C. §371 corresponding to International Application Ser. No. PCT/FR97/02270, filed Dec. 11, 1997, which claims priority of French Patent Application Ser. No. FR 96 15384, filed Dec. 13, 1996.

The present invention relates to novel derivatives of indolin-2-one, to a process for their preparation and to pharmaceutical compositions containing them. These novel derivatives are generally endowed with an affinity for vasopressin and/or oxytocin receptors and can thus constitute active principles of pharmaceutical compositions.

Vasopressin is a hormone known particularly for its anti-diuretic effect and its effect in arterial pressure regulation. It stimulates a number of types of receptors: $V_1$ ($V_{1a}$, $V_{1b}$ or $V_2$). Those receptors are located in the liver, vessels (coronary, renal, cerebral), platelets, kidneys, uterus, pancreas, adrenal glands, central nervous system and the pituitary gland. Oxytocin has a peptide structure which is close to that of vasopressin. Oxytocin receptors are also found in the smooth muscle of the uterus; they are essentially found in the myoepithelial cells of the mammary gland, in the central nervous system, in the kidneys, in the vessels and in the adipocytes. The location of the different receptors are described in: Jard S. et al., "Vasopressin and oxytocin receptors: and overview, in progress" in Endocrinology; Imura H. and Shizurne K., eds., Experta Medica, Amsterdam, 1988, 1183–1188, and in the following articles: Presse Médicale, 1987, 16 (10), 481–485, J. Lab. Clin. Med., 1989, 114 (6), 617–632 and Pharmacol. Rev., 1991 43 (1), 73–108. Vasopressin thus has hormonal, cardiovascular, hepatic, renal, antidiuretic, aggregating and effects on the central and peripheral nervous systems, on the uterine and intestinal spheres and the occular and pulmonary system. Oxytocin intervenes in parturition, lactation, sexual behaviour and in the regulation of fat metabolism.

Antagonists for the $V_2$ receptors of vasopressin (also known as AVP-2-antagonists or $V_2$ antagonists) can be recommended as powerful aquaretics which specifically intervene in renal re-absorption of water without causing electrolyte loss ($Na^+$, $K^+$) unlike diuretics which are conventionally used in clinical medicine, such as furosemide or hydrochlorothiazide. These latter cause hypokalemia and hyponatremia after prolonged treatment.

The first antagonist for the $V_2$ receptors of arginine-vasopressin (hereinafter termed AVP), OPC-31260, is currently under clinical development. A comparison of the effects of OPC-31260 with conventional diuretics such as furosemide shows that both in animals (Yoshitaka Y. et al., Br. J. Pharmacol., 1992, 105, 787–791) and in man (Akihiro O. et al., J. Clin. Invest., 1993, 92, 2653–2659, Akihiro O. et al., J. Pharmacol. Exp. Ther., 1995, 272, 546–551), such a composition selectively favours aqueous diuresis and does not affect ion excretion, or only has a slight effect in high doses.

Indolin-2-one derivatives have been described in the literature. By way of example, the patent ZA 830952 describes derivatives for use as antihypertensors which inhibit the conversion enzyme, and French patent FR 1 509 373 which describes diuretic compounds endowed with an effect on potassium excretion.

A number of patent applications or patents also describe a series of non peptide compounds with an affinity for vasopressin and/or oxytocin receptors. This is the case, for example in European patent EP 382 185 which describes carbostyryl derivatives which are antagonists of vasopressin for use as vasodilators, hypotensors, diuretics and anti-platelet aggregating agents; EP 444 945 which describes spiropiperidine derivatives for use, notably, in dysmenorrhea; EP 514 667 which describes benzazepine derivatives for use, notably, in renal function disorders, in hyponatremia, diabetes or in the treatment and prophylaxis of hypertension and in inhibition of platelet aggregation; or in Japanese patent JP 03127732 which describes indole derivatives as vasopressin antagonists. Benzyl- or sulfonylindoline and indole derivatives have also been described as antagonists for vasopressin and/or oxytocin. In this regard, the following documents can be cited: EP 469 984, EP 526 348, EP 636 608, EP 636 609, and International patent applications WO 93/15051 and WO 95/18105.

It has now been discovered that certain indolinones have an excellent affinity for the receptors of vasopressin and/or oxytocin. These novel indolin-2-ones are powerful antagonists for the $V_2$ receptors of vasopressin and possibly for oxytocin receptors. Further, depending on their structure and in particular the presence of various polar functions, in particular functions which can form salts, these molecules have good dispersibility and/or solubility in water which endows then with an improved pharmacological activity and excellent bio-availability and also enables injectable galenical forms to be prepared easily.

Thus in one of its aspects, the present invention relates to indolin-2-ones with formula

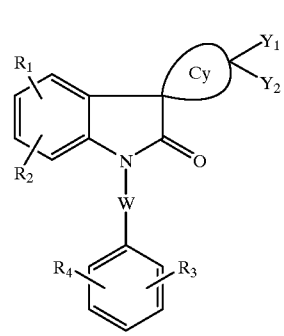

(I)

where:

$R_1$ and $R_2$ each independently represent hydrogen; a hydroxyl; a halogen; a ($C_1$–$C_7$)alkyl; a ($C_1$–$C_7$) polyfluoroalkyl; a ($C_1$–$C_7$)alkoxy; a ($C_1$–$C_7$)alkylthio; a ($C_1$–$C_7$)polyfluoroalkoxy; a ($C_3$–$C_7$)cycloalkyloxy; a ($C_3$–$C_7$)cycloalkylthio; a cycloalkylmethoxy or a cycloalkylmethylthio in which the cycloalkyl is $C_3$–$C_7$; a phenoxy; a benzyloxy; nitro; cyano;

$R_3$ and $R_4$, independently of each other, substitute the phenyl group one or more times and each independently represent hydrogen; a halogen; a ($C_1$–$C_7$)alkyl; a $C_2$–$C_7$)alkenyl; a ($C_1$–$C_7$)polyhalogenoalkyl; a phenyl or a benzyl; a cyano; a nitro; a —$NR_5R_6$ group; hydroxyamino; hydroxyl; an $OR_7$ group; a $SR_7$ group; a —$COOR_8$ group; a —$CONR_9R_{10}$ group; a —$CSNR_9R_{10}$ group, at least one of radicals $R_3$ and $R_4$ being other than hydrogen; $R_5$ and $R_6$ each independently represent hydrogen; a ($C_1$–$C_7$)alkyl; a ($C_2$–$C_7$) alkenyl; a phenyl; a benzyl; a ($C_1$–$C_7$)alkylcarbonyl; a ($C_1$–$C_7$)alkylthiocarbonyl carbonyl; a $C_3$–$C_7$) cycloalkylcarbonyl; a $C_3$–$C_7$)cycloalkylthiocarbonyl; a benzoyl; a thienylcarbonyl; a furylcarbonyl; a ($C_1$–$C_7$) alkyloxycarbonyl; a phenoxycarbonyl; a benzyloxycarbonyl; a carbamoyl or a thiocarbamoyl not substituted or substituted by $R_9$ and $R_{10}$, or $R_5$ and $R_6$ together with the nitrogen to which they are bonded constitute a heterocyclic group selected from pyrrolidine, pyrroline, pyrrole, indoline, indole or piperidine groups; or $R_5$ together with the nitrogen atom to which it is bonded and the carbon atom adjacent to the phenyl group constitutes a heterocycle selected from indole, indoline and tetrahydroquinoline, and $R_6$ represents hydrogen; a ($C_1$–$C_7$)alkyl; a benzyl; a ($C_1$–$C_7$)alkylcarbonyl; a ($C_1$–$C_7$)thiocarbonyl; a $C_3$–$C_7$)cyclo-alkylcarbonyl; a $C_3$–$C_7$)cycloalkylthiocarbonyl; ($C_1$–$C_7$)alkyloxycarbonyl; a phenoxycarbonyl; a benzyloxycarbonyl; a carbamoyl or a thiocarbamoyl group not substituted or substituted by $R_9$ and $R_{10}$;

$R_7$ represents a ($C_1$–$C_7$)alkyl; a ($C_2$–$C_7$)alkenyl; a phenyl; a benzyl; a ($C_3$–$C_7$)cycloalkyl; a ($C_1$–$C_7$) polyfluoroalkyl; a formyl; a ($C_1$–$C_7$)alkylcarbonyl; a benzoyl; a benzylcarbonyl;

$R_8$ represents hydrogen; a ($C_1$–$C_7$)alkyl; a phenyl; a benzyl;

$R_9$ and $R_{10}$ each independently represent hydrogen; a ($C_1$–$C_7$)alkyl; a ($C_1$–$C_7$)polyfluoroalkyl; a ($C_2$–$C_7$) alkenyl; a $C_3$–$C_7$)cycloalkyl optionally substituted by a hydroxy($C_1$–$C_4$)alkyl group; a pyridyl; a phenyl; a thienyl; a furyl; or $R_9$ and $R_{10}$ together with the nitrogen atom to which they are bonded constitute a heterocyclic group selected from pyrrolidine, piperidine or piperazine groups not substituted or substituted by one or more ($C_1$–$C_4$)alkyl group(s); and the ($C_6$–$C_7$) azacycloalkyl group;

W represents a —$CH_2$— or —$SO_2$— group;

Cy constitutes, together with the carbon atom to which it is bonded, a non aromatic, saturated or unsaturated $C_5$–$C_{12}$ hydrocarbon cycle, optionally condensed or substituted by one or more ($C_1$–$C_7$)alkyl group(s), said groups possibly substituting the same carbon atom one or more times, or by a $C_3$–$C_6$ spirocycloalkyl group;

$Y_1$ and $Y_2$ substitute the same carbon atom of Cy, and $Y_1$ represents either
(i) a ($C_0$–$C_4$)alkylene-T—Z group,
(ii) a ($C_0$–$C_3$)alkylene —$NR_{16}$—T—Z group in which $R_{16}$ represents a hydrogen atom, a ($C_1$–$C_3$)alkyl, an oxygen atom, the nitrogen atom carrying the $R_{16}$ optionally being quaternary, with the counter-anion then being $Cl^-$, $Br^-$, $I^-$ or $CH_3SO_4^-$;
(iii) a ($C_1$–$C_3$)alkylene-O—T—Z group,
(iv) a ($C_0$–$C_3$)alkylene-S—T—Z group,
a ($C_0$–$C_3$)alkylene-SO—T—Z group,
a ($C_0$–$C_3$)alkylene-$SO_2$—T—Z group, $Y_2$ represents a hydrogen atom or a hydroxyl group or forms with $Y_1$ a ($C_1$–$C_4$)alkylidene-T—Z group, a ($C_2$–$C_3$)alkylidene —$NR_{16}$—T—Z group in which $R_{16}$ is as defined above or a ($C_2$–$C_3$)alkylidene-O—T—Z group, or together with $Y_1$ forms a spiro-5-dihydro-3H-furan-2-one, T represents ($C_1$–$C_4$)alkylene optionally interrupted by a ($C_3$–$C_6$)cyclo-alkylene, said alkylenes optionally being substituted one or more times on the same carbon atom by a ($C_1$–$C_3$)alkyl group; or T represents a direct bond;

Z represents hydroxyl; benzyloxy; a —$NR_{11}R_{12}$ group; —$^+NR_{11}R_{12}$($C_1$–$C_4$)alkyl ($A^-$), ($A^-$) being $Cl^-$, $Br^-$, $I^-$ or $CH_3SO_4^-$; —$N(O)R_{11}R_{12}$; a —$COOR_{11}$ group; a —$NR_{11}COR_{12}$ group; benzyloxycarbonylamino; a —$CONR_{11}R_{12}$ group it being understood that:

when $Y_1$ is as defined in cases (ii), (iii) and (iv) and when T represents a methylene group or a direct bond, Z cannot be a hydroxyl; a benzyloxy; —$NR_{11}R_{12}$; $N(O)R_{11}R_{12}$; —$^+NR_{11}R_{12}$($C_1$–$C_4$) alkyl; —$NR_{11}COR_{12}$; benzyl-oxycarbonylamino group, or when $Y_1$=Z, Z cannot be a hydroxyl or a benzyloxy group;

$R_{11}$ and $R_{12}$ each independently represent hydrogen; a ($C_1$–$C_7$)alkyl; a ($C_1$–$C_4$)alkoxy; a ($C_1$–$C_3$)alkylane substituted by a ($C_3$–$C_7$)cycloalkyl or phenyl group, said groups optionally being mono or polysubstituted by $R_{13}$; or $R_{11}$ and $R_{12}$, together with the nitrogen atom to which they are bonded, optionally constitute a heterocycle selected from the heterocycles: azetidine, pyrrolidine, piperidine, piperazine, piperazinone, morpholine, morpholinone, thiomorpholine, hexahydroazepine optionally mono- or poly-substituted by $R_{13}$; or a thiomorpholine-1,1-dioxide or a thiomorpholine-1-oxide; or $R_{12}$ represents pyrrolidone or piperidone;

$R_{13}$ represents a hydroxyl group; a ($C_1$–$C_4$)alkyl; a ($C_1$–$C_4$)alkoxy; a mercapto; a ($C_1$–$C_4$)alkylthio; a ($C_1$–$C_4$)alkylsulfinyl; a ($C_1$–$C_4$)alkylsulfonyl; a benzyloxy or a hydroxyalkyloxy group; a $NR_{14}R_{15}$ group where $R_{14}$ and $R_{15}$ each independently represent hydrogen or a ($C_1$–$C_4$)alkyl or a ($C_1$–$C_4$) alkyl-oxycarbonyl or a benzyloxycarbonyl group; a carboxy; a ($C_1$–$C_4$) alkyl-oxycarbonyl, a phenoxycarbonyl; a benzyloxycarbonyl; a carbamoyl; an amidino; a guanidino; an imidazolyl; a thienyl; a pyridyl; an indolyl; a tetrahydroisoquinolyl group; and their salts, solvates or hydrates.

A preferred family of compounds with formula (I) is represented by formula (Ip)

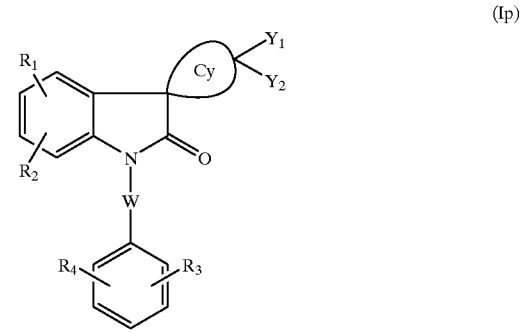

(Ip)

where:

$R_1$ and $R_2$ each independently represent hydrogen; a hydroxyl; a halogen; a ($C_1$–$C_7$)alkyl; a ($C_1$–$C_7$) polyfluoroalkyl; a ($C_1$–$C_7$)alkoxy; a ($C_1$–$C_7$)alkylthio; a $C_1$–$C_7$)polyfluoroalkoxy; a ($C_3$–$C_7$)cycloalkyloxy; a ($C_3$–$C_7$) cycloalkylthio; a cycloalkylmethoxy or a cycloalkylmethylthio in which the cycloalkyl is $C_3$–$C_7$; a phenoxy; a benzyloxy; a nitro; a cyano;

$R_3$ and $R_4$ independently of each other substitute the phenyl group one or more times and each independently represent a hydrogen; a halogen; a $C_1$–$C_7$)alkyl; a ($C_2$–$C_7$)alkenyl; a ($C_1$–$C_7$)polyhalogenoalkyl; a phenyl or a benzyl; a cyano; a nitro; a —$NR_5R_6$ group; a hydroxyamino; a hydroxyl; an $OR_7$ group; a $SR_7$ group; a —$COOR_8$ group; a —$CONR_9R_{10}$ group; a —$CSNR_9R_{10}$ group, at least one of radicals $R_3$ and $R_4$ being other than hydrogen;

$R_5$ and $R_6$ each independently represent hydrogen; a $(C_1-C_7)$alkyl; a $(C_2-C_7)$alkenyl; a phenyl; a benzyl; a $(C_1-C_7)$alkylcarbonyl; a $(_1-C_2)$alkylthiocarbonyl; a $(C_3-C_7)$cycloalkylcarbonyl; a $(C_3-C_7)$ cycloalkylthiocarbonyl; a benzoyl; a thienylcarbonyl; a furylcarbonyl; a $(C_1-C_7)$alkyloxycarbonyl; a phenoxycarbonyl; a benzyloxycarbonyl; a carbamoyl or a thiocarbamoyl substituted or not substituted by $R_9$ and $R_{10}$, or $R_5$ and $R_6$ together with the nitrogen atom to which they are bonded constitute a heterocyclic group selected from the following groups: pyrrolidine, pyrroline, pyrrole, indoline, indole, piperidine; or $R_5$ together with the nitrogen atom to which it is bonded and the carbon atom adjacent to the phenyl group constitute a heterocycle selected from indole, indoline and tetrahydroquinoline and $R_6$ represents hydrogen; a $C_1-C_7$)alkyl; a benzyl; a $(C_1-C_7)$alkylcarbonyl; a $(C_1-C_7)$ alkylthiocarbonyl; a $C_3-C_7$)cycloalkylcarbonyl; a $(C_3-C_7)$cycloalkylthiocarbonyl; a $(C_1-C_7)$alkyloxycarbonyl; a phenoxycarbonyl; a benzyloxycarbonyl; a carbamoyl or a thiocarbamoyl group not substituted or substituted by $R_9$ and $R_{10}$;

$R_7$ represents a $(C_1-C_7)$alkyl; a $(C_2-C_7)$alkenyl; a phenyl; a benzyl; a $(C_3-C_7)$cycloalkyl; a $(C_1-C_7)$ polyfluoroalkyl; a formyl; a $(C_1-C_7)$alkylcarbonyl; a benzoyl; a benzylcarbonyl;

$R_8$ represents hydrogen, a $(C_1-C_7)$alkyl; a phenyl; a benzyl;

$R_9$ and $R_{10}$ each independently represent hydrogen; a $(C_1-C_7)$alkyl; a $(C_1-C_7)$polyfluoroalkyl; a $(C_2-C_7)$ alkenyl; a $(C_3-C_7)$cycloalkyl optionally substituted by a hydroxy$(C_1-C_4)$alkyl group; a pyridyl; a phenyl; a thienyl; a furyl; or $R_9$ and $R_{10}$ together with the nitrogen atom to which they are bonded constitute a heterocyclic group selected from the following groups: pyrrolidine, piperidine or piperazine substituted or not substituted by $(C_1-C_4)$alkyl groups; and the $(C_6-C_7)$ azacycloalkyl group;

W represents a —$CH_2$— or —$SO_2$— group;

Cy, together with the carbon atom to which it is bonded, constitutes a non aromatic, saturated or unsaturated $C_5-C_{12}$ group, optionally condensed or substituted by one or more $(C_1-C_7)$alkyl groups, said groups possibly being substituted one or more times on the same carbon atom or by a $C_3-C_6$ spirocycloalkyl group;

$Y_1$ and $Y_2$ substitute the same carbon atom of Cy, and $Y_1$ represents either (i) a $(C_0-C_4)$alkylene —T—Z group, (ii) a $(C_0-C_3)$alkylene —$NR_{16}$—T—Z group where $R_{16}$ represents a hydrogen atom, a $(C_1-C_3)$alkyl, an oxygen atom, the nitrogen atom carrying the $R_{16}$ optionally being quaternary, the counter-anion then being as defined in Z, (iii) a $(C_1-C_3)$alkylene -O—T—Z group, T and Z being as defined below, $Y_2$ represents a hydrogen atom or a hydroxyl group or forms a double bond forms with $Y_1$a $(C_1-C_4)$ alkylidene—T—Z group, a $(C_2-C_3)$ alkylidene —$NR_{16}$—T—Z group in which $R_{16}$ is as defined above or a $(C_2-C_3)$alkylidene-O—T—Z group, T represents a $(C_1-C_4)$alkylene group optionally interrupted by a $(C_3-C_6)$cycloalkylene group, said alkylenes optionally being substituted one or more times on the same carbon atom by a $(C_1-C_3)$alkyl group; or T represents a direct bond;

Z represents a —$NR_{11}R_{12}$ group; a —$^+NR_{11}R_{12}(C_1-C_4)$ alkyl $(A^-)$, $(A^-)$ being an $Cl^-$, $Br^-$, $I^-$ or $CH_3SO_4^-$; a —$N(O)R_{1112}$; a —$COOR_{11}$ group; a —$NR_{11}COR_{12}$ group; a benzyloxy-carbonylamino; or a —$CONR_{11}R_{12}$ group, it being understood that when $Y_1$ is as defined in case (ii) and (iii) and when T represents a methylene group or a direct bond, then Z cannot be a —$NR_{11}R_{12}$; a —$^+NR_{11}R_{12}$; a $(C_1-C_4)$alkyl; a —$NR_{11}COR_{12}$; or a benzyloxycarbonylamino group;

$R_{11}$ and $R_{12}$ each independently represent hydrogen; a $(C_1-C_7)$alkyl; a $(C_1-C_7)$alkoxy; a $(C_3-C_7)$cycloalkyl; a phenyl; a $(C_1-C_3)$alkylenecycloalkyl where the cycloalkyl is $C_3-C_7$, a $(C_1-C_3)$alkylenephenyl, said groups optionally being mono or polysubstituted by $R_{13}$; or $R_{11}$ and $R_{12}$ with the nitrogen atom to which they are bonded optionally constitute a heterocycle selected from the heterocycles: azetidine, pyrrolidine, piperidine, piperazine, piperazinone, morpholine, morpholinone, thiomorpholine, hexahydroazepine optionally mono or poly-substituted by $R_{13}$; or a thiomorpholine-1,1-dioxide or a thiomorpholine-1-oxide; or $R_{12}$ represents a pyrrolidone or a piperidone;

$R_{13}$ represents a hydroxyl group; a $(C_1-C_4)$alkyl; a $(C_1-C_4)$alkoxy; a mercapto; a $(C_1-C_4)$alkylthio; a $(C_1-C_4)$alkylsulfinyl; a $(C_1-C_4)$alkylsulfonyl; a benzyloxy or a hydroxyalkyloxy; a $NR_{14}R_{15}$ group where $R_{14}$ and $R_{15}$ each independently represent hydrogen or a $(C_1-C_4)$alkyl or a $(C_1-C_4)$ alkyloxycarbonyl or a benzyloxycarbonyl; a carboxyl group; a $(C_1-C_4)$ alkyloxycarbonyl, a phenoxycarbonyl; a benzyloxycarbonyl; a carbamoyl; an amidino; a guanidino; an imidazolyl; a thienyl; a pyridyl; an indolyl; or a tetrahydroiso-quinolyl group;

and their salts, solvates or hydrates.

Compounds with formula (IA):

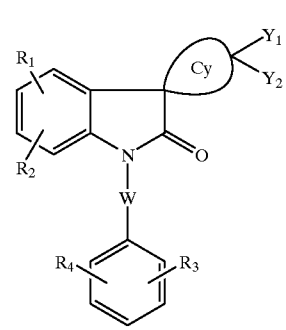

(IA)

where substituent $R_1$ is in the 5 position of the indolin-2-one, $R_2$ represents hydrogen and Cy, $Y_1$, $Y_2$, $R_3$, $R_4$ and W are as defined for (I) are preferred compounds, along with their salts, hydrates or solvates.

Of these compounds, compounds in which Cy represents a cyclohexyl, $Y_1$ and $Y_2$ substitute the 4 position of the cyclohexyl; $R_1$ represents a chlorine atom or an ethoxy group; W represents $SO_2$; $R_3$ and $R_4$ are as defined for (I), and their salts, hydrates or solvates, are preferred.

Particularly preferred compounds from the above are those in which $Y_1$ is:

either a $(C_0-C_4)$alkylene-T—Z group where Z is a —$NR_{11}R_{12}$ group; a -$CONR_{11}R_{12}$; a $COOR_{11}$ group and T is a direct bond or a ($C_1$–$C_4$)alkyl group, preferably a direct bond;

or a ($C_0$–$C_3$)alkylene—$NR_{16}$—T—Z group where T is a ($C_1$–$C_4$)alkylene group and Z is a —$NR_{11}R_{12}$ group;

or a ($C_0$–$C_3$)alkylene-S—T—Z group where T is a ($C_1$–$C_4$)alkylene group and Z is a —$NR_{11}R_{12}$ group.

In the present invention, the terms "($C_1$–$C_7$)alkyl, $C_1$–$C_7$) alkylene, ($C_1$–$C_7$)alkylidene" mean a straight or branched chain alkyl, alkylene or alkylidene group containing 1 to 7 carbon atoms.

Non aromatic $C_5$–$C_{12}$ hydrocarbon cycles include condensed or bridged, saturated or unsaturated mono- or polycyclic radicals, which may be terpenic. These radicals are optionally mono- or poly-substituted by a ($C_1$–$C_4$)alkyl group. Monocyclic radicals include cycloalkyls, for example cyclopentyl, cyclohexyl, cycloheptyl, cyclooctyl, cyclododecyl. Polycyclic radicals include, for example, norbornane, adamantane, hexahydroindane, norbornene, dihydrophenalene, bicyclo [2.2.1]heptane, bicyclo [3.3.1] nonane; tricyclo [$5.2.1.0^{2,6}$]decane.

The phenyl group in substituent $R_1$, $R_2$, $R_3$, $R_4$, $R_5$, $R_6$, $R_7$, $R_8$, $R_9$, $R_{10}$, $R_{11}$ and $R_{12}$ can be non substituted, mono- or disubstituted with a ($C_1$–$C_7$)alkyl, preferably methyl, a trifluoromethyl, a ($C_1$–$C_7$)alkoxy, preferably methoxy or ethoxy, a halogen or trisubstituted by a ($C_1$–$C_7$)alkyl, a ($C_1$–$C_7$)alkoxy or a halogen.

In the present invention, the term halogen means an atom selected from fluorine, chlorine, bromine or iodine, preferably fluorine or chlorine.

When a compound of the invention includes one or more asymmetric carbons, the optical isomers of that compound form an integral part of the invention.

When a compound of the invention is stereoisometric, for example axial equatorial or Z-E, the invention encompasses all stereoisomers of this compound.

Salts of compounds with formula (I) of the present invention include those with mineral or organic acids which enable compounds with formula (I) to be separated or crystallized as appropriate, examples being picric acid, oxalic acid or an optically active acid, for example a tartric acid, a dibenzoyltartric acid, a mandelic acid or a camphorsulfonic acid, and those which form physiologically acceptable salts such as the hydrochloride, hydrobromide, sulfate, hydrogenophosphate, dihydrogenophosphate, maleate, fumarate, 2-naphtalenesulfonate, or paratoluenesulfonate.

Salts of compounds with formula (I) also include salts with organic or mineral bases, for example salts of alkali or alkaline-earth metals, such as sodium, potassium, or calcium salts, sodium and potassium salts being preferred, or with an amine such as trometamol, or salts of arginine, lysine, or any other physiologically acceptable amine.

The functional groups which may be present in the molecule of compounds with formula (I) and in the reaction intermediates can be protected, either permanently or temporarily, by protective groups which ensure univocal synthesis of the expected compounds.

The term "temporary protective group for amines, alcohols, phenols, thiols or carboxylic acids" means protective groups such as those described in Protective Groups in Organic Synthesis, Greene T. W. and Wuts P. G. M., ed. John Wiley & Sons, 1991 and in Protective Groups, Kocienski P. J., 1994, Georg Thieme Verlag.

Examples of temporary protective groups for amines are benzyls, carbamates (such as tert-butyloxycarbonyl which can be cleaved in an acid medium, or benzyloxycarbonyl which can be cleaved by hydrogenolysis), carboxylic acids (alkyl esters such as methyl or ethyl, tert-butyl hydrolysable in basic or acidic media, hydrogenolysable benzylic groups), alcohols or phenols such as tetrahydropyranyl, methyloxymethyl or methylethoxymethyl, tert-butyl and benzyl ethers. Reference should be made to the well known general methods described in Protective Groups, cited above.

Permanent protective groups are those which are stable under the cleaving conditions cited above and which are capable of being present in the final products. Such O-protective or N-protective groups are constituted by ($C_1$–$C_7$)alkyl and phenyl groups. Permanent N-protective groups also include ($C_1$–$C_5$)alkanoyl groups and aroyl groups such as the benzoyl group.

Compounds (I) can comprise precursor groups for other functions which are subsequently generated in one or more further steps.

In the present invention, it is preferable to use temporary protective groups which can be cleaved in an acid medium, or in a neutral medium by hydrogenolysis.

Compounds with formula (I) in which the various polar functions, in particular functions which can form salts which improve the solubility and/or dispersibility in water, are preferably carried by the $Y_1$ group.

The present invention also relates to a process for preparing compounds with formula (I). The compounds of the invention can be prepared in accordance with SCHEME 1 below:

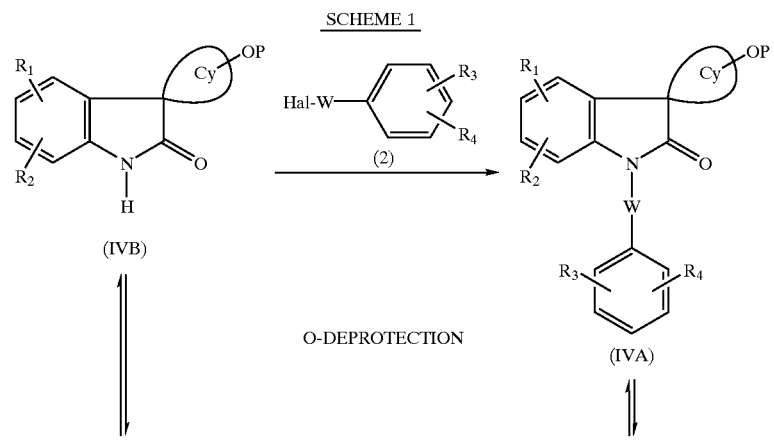

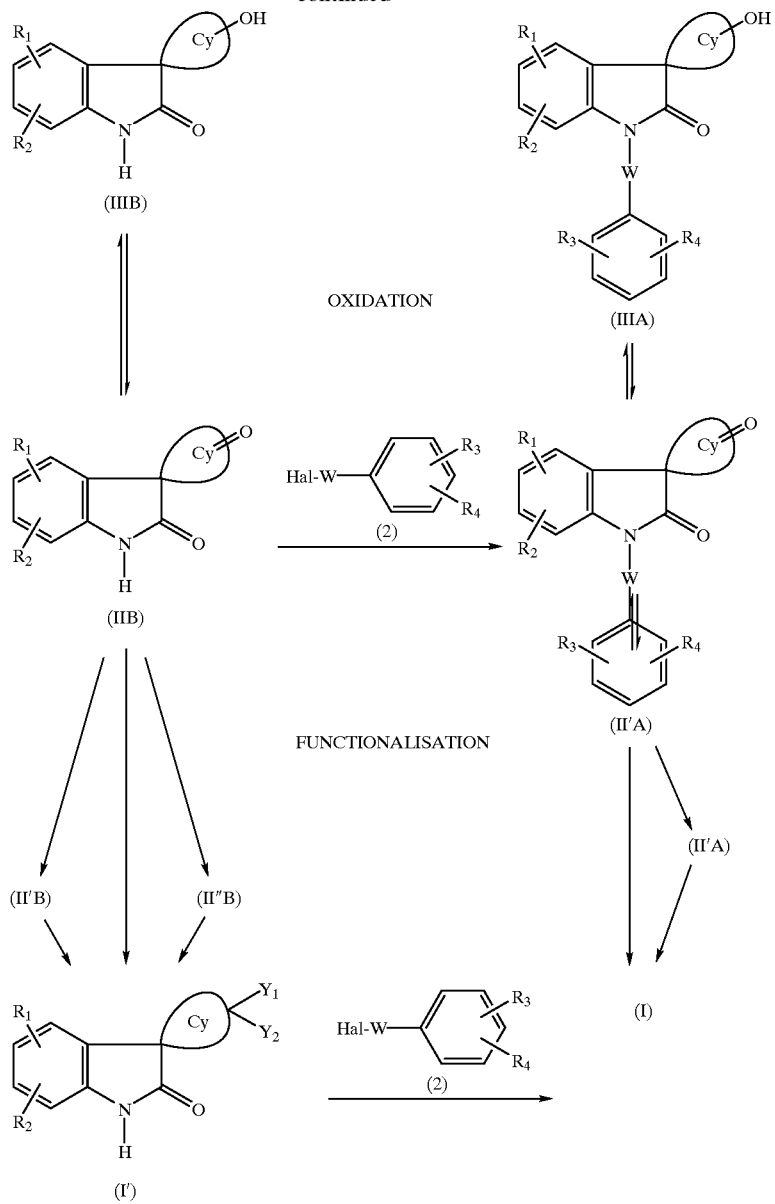
In Scheme 1 above, compounds (II'A) or (II'B) are compounds with the following formula:
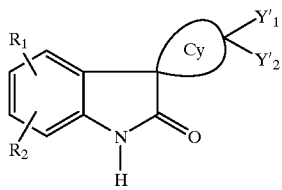
(II'B)
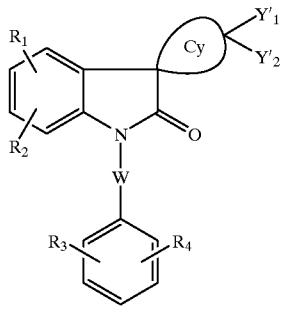
(II'A)

where $Y'_1$ and $Y'_2$ represent $Y_1$ and/or $Y_2$ or a precursor of $Y_1$ and/or $Y_2$.

Preferably, $Y'_1$ is one of the following groups:
(i) a $(C_0-C_4)$alkylene-X group,
(ii) a $(C_0-C_3)$alkylene-X group,
(iii) a $(C_1-C_3)$alkylene-X group,
(iv) a $(C_0-C_3)$alkylene-X group or forms with $Y'_2$ a $(C_1-C_4)$alkylidene-X group or a $(C_2-C_3)$alkylidene-X group, where X represents hydroxyl, a $(C_1-C_3)$alkoxy, a halide, a sulfonic acid ester such as tosyloxy or mesyloxy, a cyano, an azido, a nitro or together with the alkylene or alkylidene group to which it is bonded, constitutes an aldehyde or a ketone.

Compound (II"B) has the following formula:

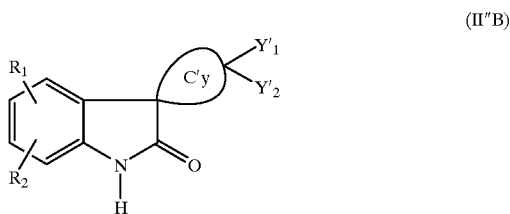

(II"B)

where C'y, together with the carbon to which it is bonded, constitutes an unsaturated carbon cycle.

The present invention also relates to a process for preparing compounds with formula (I), characterized in that:

1) a compound with formula (I'):

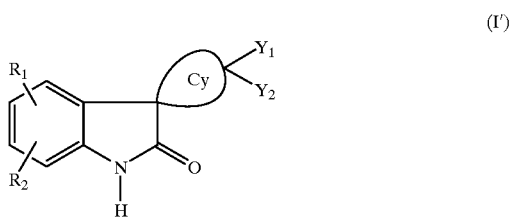

(I')

where $R_1$, $R_2$, Cy, $Y_1$ and $Y_2$ are as defined for (I), is reacted with a compound with formula:

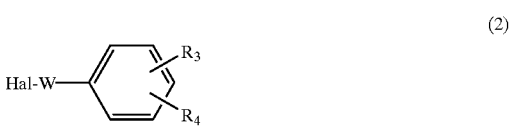

(2)

where W, $R_3$ and $R_4$ are as defined for (I) and Hal represents a halogen atom, in the presence of a metal hydride such as sodium hydride or an alkaline alcoholate such as potassium tert-butoxide at temperatures comprised between −40° C. and 25° C., in an anhydrous solvent such as tetrahydrofuran 2) or a number of nucleophilic reagents such as thiols, amines, or carbanions can be reacted with carbonyl derivatives (IIA) in very general reactions which are well known to the skilled person to directly produce compounds (I) of the invention or intermediate compounds (II'A) which can be transformed into (I) in one or more steps.

In the present description, the step transforming (IIA) into (I) or (II'A) is termed the "functionalisation step" which is of the same nature as that which transforms compounds (IIB) into compounds (I'), (II'B) or (II"B). These transformations will be described together below. The skilled person can select from compounds (IIA) and (IIB) those which can undergo the functionalisation step depending on the reactions carried out. As an example, reduction reactions using reducing agents such as sodium borohydride or hydrolyses in a basic medium will rather be carried out using compounds (IIB); reactions using carbanions will preferably be carried out on compounds (IIA) or managed to take into account the lactame function of compounds (IIB), for example by protecting it.

Very generally, compounds with formula (I) or (I') and intermediates with formulae (II'A) and (II'B) can be prepared by homologation reactions, i.e., conventional carbon-carbon coupling from carbonyl derivatives (IIA) and (IB) respectively. The methods described in Synthesis, 1979, 633–665 which are applicable to the invention can be consulted in this respect.

Compounds (I) or (I'), (II'A) or (II'B) in which $Y_1+Y_2$ form a $(C_1-C_4)$alkylidene-T—Z, a $(C_1-C_3)$alkylidene —$NR_{16}$—T—Z or a $(C_1-C_3)$ alkylidene-O—T—Z group are advantageously prepared by reacting phosphorous derivatives such as phosphonium ylides, phosphine oxide anions or phosphonates with carbonyl derivatives (IIA) or (IIB) these reactions are known as Wittig, Wittig-Horner or Horner-Wadworth-Emmons reactions and have been widely described and demonstrated in the literature. The following can be consulted in this regard: Org. Reactions, 1965, 14, 270; Chem. Organophosphorus Compounds, 1994, 185; Org. Reactions, 1977, 25, 73; Chem. Rev., 1974 and 1989, 74 and 89, 87 and 863 respectively.

Compounds (II'A) or (II'B) comprising alcohol, aldehyde or ketone functions and compounds (I) or (I') comprising carboxylic acid functions or esters can be interconverted by conventional oxidation or reduction processes which are well known to the skilled person.

Compounds (II'B) or (II'B) in which $Y'_1$ represents a cyano group are advantageously prepared by reacting carbonyl compounds (IIA) or (IIB) with tosylmethylisonitrile under the conditions described in J. Org. Chem., 1977, 42, 3114–3118.

Compounds (I) or (I') in which $Y_1$ represents a $(C_1-C_3)$ alkylene group substituted by a —$NR_{16}$—T—Z or S—T—Z group can be prepared by conventional reactions using compounds (II'A) or (II'B) where $Y'_1$ represents the same alkylene group substituted with a group X, X being defined as a nucleophobic group such as a halogen, preferably bromine, chlorine or iodine, or a sulfonic acid derivative such as tosyloxy, mesyloxy, with a $HNR_{16}$—T—Z or HS—T—Z amine respectively, in polar solvents such as dimethylformamide, tetrahydrofuran or acetonitrile at temperatures in the range 0° C. to 120° C. X can also represent an azido group which can be reduced to an amine group. Compounds (II'A) or (II'B) comprising X as defined above are generally prepared from the corresponding alcohols. For example, one can refer to triphenylphosphine/carbon tetrachloride systems as described in Angew. Chem. Int. Ed., 1975, 14, 801 or triphenylphosphine/$C(Hal)_4$ systems where Hal represents a halogen in the presence of pyridine, as described in Carbohyd. Res., 1978, 61, 511, or by reaction with an aryl- or alkylsulfonyl halide in the presence of a base in a neutral solvent. Groups X can be exchanged: as an example, a sulfonate group can be transformed into a halide such as an iodine derivative by reaction with an alkaline iodide such as sodium iodide as described in J. Chem. Soc., 1949, 326. When X represents a halogen, it can be transformed into a hydroxyl by substitution with a nitrate ion which is then reduced in the presence of a metallic catalyst such as palladium on carbon as described in J. Med. Chem., 1995, 38, 130–136.

Reducing amination reactions, consisting of reacting an amine with a carbonyl derivative (IIA), (IIB), (II'A) or (II'B) in an acidic medium in the presence of a reducing agent, can also be used. The reducing agent can be hydrogen in the presence of a metallic catalyst such as palladium, Raney nickel (see M. Freifelder in "Practical Hydrogenations in Organic Synthesis, Procedures and Commentary", John Wiley & Sons, New York, 1978, Chapter 10) or hydrides such as $BH_3$, alkaline borohydrides or its derivatives such as sodium cyanoborohydride in the presence of acetic acid (Org. Prep. Proc. Int., 1985, 17, 317) and more particularly sodium triacetoxyborohydride under the conditions described in Tetrah. Lett., 1990, 5595 or J. Org. Chem., 1996, 61, 3849–3862.

Amines can also be prepared by reducing derivatives (II'A) or (II'B) in known reactions, where X represents a nitro, azido or cyano, in the presence, for example, of hydrogen and a metallic catalyst such as palladium on carbon or platinum oxide.

Compounds (I') can be prepared in which $Y_1$ represents a $(C_1-C_3)$alkylene-O—T—Z or $Y_1+Y_2$ represent a $(C_2-C_3)$ alkylidene-O—T—Z group by reducing acetals (II'B) which are themselves obtained from an aldehyde or ketone and an HO—T—Z alcohol using methods which are well known to the skilled person, as described, for example, in J. Org. Chem., 1987, 52, 2594–2596.

Compounds (I') can be prepared in which $Y_1$ represents an S—T—Z group from thioethers of enol (II"B) by hydrogenation in the presence of a metallic catalyst such as palladium on carbon. These compounds (II"B) are themselves obtained from compounds (IIB) and HS—T—Z in the presence, for example, of rifluoroborane etherate in a chlorine-containing solvent such as dichloromethane.

Compounds (I') in which $Y_1+Y_2$ form a spiro-5-dihydro-3H-furan-2-one can be prepared as described in J. Chem. Soc. , Chem. Commun. 1986, 624–625 from compounds (IIB) and methyl acrylate in the presence of samarium iodide followed by acid treatment. The action of an $HNR_{11}R_{12}$ amine on these compounds (I') enables the spirolactone to open, and compound (I') is obtained where $Y_2$=OH and $Y_1$=$(CH_2)_2CONR_{11}R_{12}$.

An alternative to synthesis of compounds (I) where $Y_1$ represents a $(C_1-C_3)$alkylene-O—T—Z group (case (iii)) in which T represents —$CH_2$— and Z represents a —$COOZ_1$ group in $Z_1$ represents hydrogen, a $(C_1-C_3)$alkyl or a benzyl group, consists of using the corresponding alcohols which are reacted with a powerful alkylating reactant such as a trifluoromethane sulfonate with formula $CF_3SO_2O$—$CH_2$—COO Alk, generated in situ by reacting silver triflate with the corresponding halogen-containing derivative where Alk represents a $(C_1-C_4)$alkyl group, in halogenated solvents such as dichloromethane or carbon tetrachloride, in the presence of a base such as 2,6-di-tert-butylpyridine using the method described for alkyl trifluoromethane sulfonates in Carbohydrate Research, 1975, 44, $C_5-C_7$.

Compounds with formula (I) or (I') can comprise amine or acid functions which can be transformed into amide functions by respective reactions with derivatives of acids or amines which may comprise asymmetric carbon atoms. Reference can be made in this respect to the non racemising coupling reactions which are well known to the skilled person, in particular in peptide synthesis, and to Wunsch E., in Methoden der Organischen Chemie (Synthese von Peptiden), 1974, 15, Vol 1+2, Thieme Verlag, Stuttgart, or Jones J. H., in The Peptides, 1979, 1, 65–104, Gross E., Meienhofer J., Academic Press, or Bodansky M., Principles of Peptide Synthesis and Peptide Chemistry, 1993, Springer Verlag.

Quaternary ammonium compounds, N-oxide, S-oxide derivatives and sulfones of compound (I) form part of the invention and are conventionally prepared by reaction with an alkyl halide, by oxidation with hydrogen peroxide or a peracid, such as peroxyacetic acid or metachloroperbenzoic acid in inert solvents.

Compounds (IIA) or (IIB) are prepared by oxidising the corresponding secondary alcohols (IIIA) or (IIIB) using a number of methods which are well known to the skilled person, for example, using oxidising agents such as chromium oxide in an acetic medium, or chromium oxide complexes such as pyridinium chlorochromate in inert solvents such as ethyl acetate or dichloromethane, or by hydrolysis of acetals (VA) or (VB) (see Scheme 2 below).

Compounds (IIIA) or (IIIB) can be prepared by hydrolysis of derivatives (IVA) or (IVB) in which P is a protective function of an alcohol function, for example a methoxymethyl or tetrahydropropanyl group. Hydrolysis is carried out in an acid medium, for example in the presence of hydrochloric acid in an alcohol such as methanol or ethanol, an ether such as tetrahydrofuran, at temperatures in the range −5° C. to 70° C.

Compounds (IVA) and (IVB) have been described in EP 636 608 or obtained in similar fashion.

Compounds (IIA) and (IIB) can also be obtained using SCHEME 2 below:

SCHEME 2

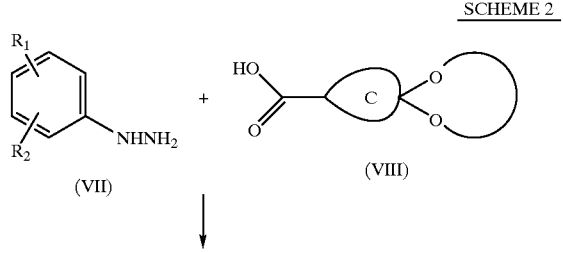

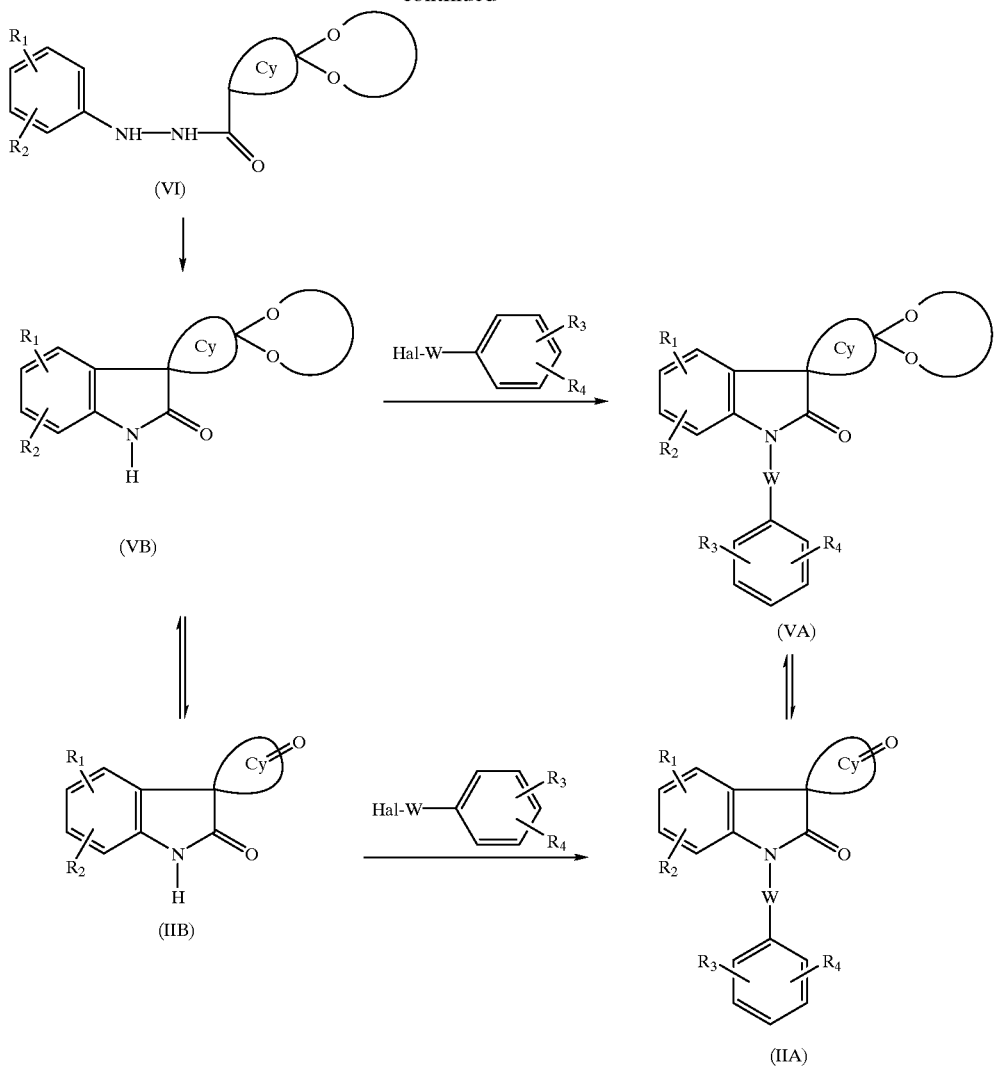

Acetals (VA) or (VB) can be obtained from the corresponding ketones (IIA) or (IIB) by reaction with a diol such as ethylene glycol or propylene glycol in a dehydrating medium but more advantageously, they can be prepared directly from the corresponding hydrazides (VI) by a Brunner reaction described by Moore R. F. et al., J. Chem. Soc., 1951, 3475–3478, for example by heating in solvents such as quinoline in the presence of a metallic or alkaline-earth oxide such as calcium oxide. It can also be heated in inert solvents such as tetraline, naphthalene or 1,2,3,4-tetramethylbenzene using the method described by Wolff J. et al., Tetrahedron, 1986, 42, (15), 4267–4272, using a lithium salt previously prepared in an inert solvent such as tetrahydrofuran at low temperature.

Phenylhydrazides (VI) can be obtained from a phenylhydrazine (VII), which are known compounds or which are prepared using known methods, and from carboxylic acid derivatives (VIII), such as esters, chlorides or mixed anhydrides obtained by reaction of an alkyl chloroformate, preferably isobutyl, in the presence of a base using conventional methods which are well known to the skilled person.

Acids (VIII) are known or prepared using known methods.

Compounds (IIA), (II'A), (IVA) and (VA) can be prepared from compounds (IIB), (II'B), (IVB) and (VB) respectively under the conditions described for preparing compounds (I) from compounds (I').

The functionalisation reactants are known compounds or can be prepared using known methods.

Reactants with formula (2):

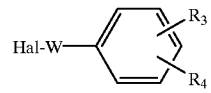

are also prepared using known methods. In particular, benzenesulfonyl halides in which $W=-SO_2-$ and $R_3$ and $R_4$ are as defined above for (I), are prepared using known methods. Thus, for example, 4-dimethylamino-benzenesulfonyl chloride is prepared as described by Sukenik C. N. et al., J. Am. Chem. Soc., 1977, 99, 851–858. More generally, benzenesulfonyl halides substituted by a dimethylamino group are known or prepared using known methods; 4-benzyl-oxybenzenesulfonyl chloride is prepared as described in EP 229 566.

The alkoxybenzenesulfonyl chloride is prepared from the sodium alkoxybenzenesulfonate, itself prepared by the action of an alkyl halide on sodium hydroxybenzenesulfonate.

Benzenesulfonyl halides are obtained as described in Col. Czechoslov. Chem. Commun., 1984, 49, 1184, from aniline derivatives substituted by the same group, said aniline derivatives themselves being obtained from the corresponding nitrated derivatives.

The benzenesulfonyl halide (2) in which the substituent in the 4 position represents a —NHCON(CH$_2$CH$_3$)$_2$ group can be prepared by the action of chlorosulfonic acid on N',N'-diethyl-N-phenylurea, itself obtained by reacting aniline with diethylcarbamoyl chloride.

When R$_3$ or R$_4$ represents an N-substituted carbamoyl group, a compound (2) in which R'$_3$ is a carboxylic acid precursor such as N-benzylcarbamoyl, can be condensed, the protective group can be deprotected by hydrogenolysis then condensed with the desired amine, or a compound (2) where R$_3$ has the expected value can be directly prepared. In general, properly chosen anilines are used as the starting point, themselves being obtained by reduction of the corresponding nitrated derivatives. The anilines are dinitrogenated under conventional conditions using nitrous acid and reacted with SO$_2$ in the presence of cupric chloride as described in J. Heterocyclic Chem., 1986, 23, 1253.

The benzyl halides in which W represents —CH$_2$— are known or are prepared using known methods. For example, one can refer to Rajanbabu J. V. , J. Org. Chem., 1986, 51, 1704–1712 and the publications cited in EP 636 609.

In general, halogenomethylbenzene derivatives can be prepared by the action of N-halogenosuccinimides on the corresponding methylbenzene derivatives and according to EP 229 566. The reaction is carried out in a solvent such as carbon tetrachloride in the presence of dibenzoyl peroxide. A halogenomethylbenzene derivative can also be prepared from a corresponding hydroxymethylbenzene derivative by the action of phosphorous tribromide in ether or by the action of thionyl chloride.

Compounds with formula (I) above also include those in which one or more hydrogen, carbon or halogen atoms, in particular chlorine or fluorine, have been replaced by their radioactive isotope, for example tritium or carbon-14. Such labeled compounds are used in metabolism or pharmacokinetics research, and constitute powerful ligands for vasopressin and/or oxytocin receptors.

The affinity of the compounds of the invention for the V$_1$ receptors of vasopressin was determined in vitro using the method described by Lynch C. J. et al., J. Biol. Chem., 1985, 260 (5), 2844–2851. That method consists of studying the displacement of tritiated vasopressin fixed to the V$_1$ sites of rat liver membranes.

Similarly, the affinity of compounds (I) of the invention for oxytocin receptors was determined in vitro by displacement of a radio-iodised analogue of oxytocin fixed to the receptors of a membranary preparation from the mammary glands of gestating rats, using a technique close to that described by Elands J. et al., in Eur. J. Pharmacol., 1987, 147, 197–207. Some compounds of the invention inhibit fixing of a radio-iodised analogue of oxytocin to the receptors of membranary preparations. Their IC$_{50}$ was low, varying between $10^{-6}$ to $10^{-9}$ M.

The affinity of compounds (I) of the invention for V$_2$ receptors was measured on a calf kidney membranary preparation using a method adapted from Crause P. et al., Molecular and Cellular Endocrinology, 1982, 28, 529–541 and Stassen F. L. et al., J. Pharmacol. Exp. Ther., 1982, 233, 50–54. The compounds of the invention inhibit fixing of tritiated arginine vasopressin to the V$_2$ receptors of the membranary preparations. The IC$_{50}$ of the compounds of the invention are low: they vary between $5 \times 10^{-7}$ and $10^{-9}$ M.

The agonist or antagonist activity of the vasopressin receptors of the compounds of the invention, administered orally, was evaluated for the normally hydrated rat (Sprague-Dawley strain) using the technique described in Br. J. Pharmacol., 1992, 105, 787–791.

The diuretic effect, generally observed for compounds with formula (I) and, for some of these compounds, in doses of 10 mg/kg or less, shows that compounds with formula (I) constitute a series of powerful V$_2$ antagonists.

The compounds of the invention are active after administration by different routes, in particular orally.

No sign of toxicity was observed using these compounds in pharmacologically active doses and their toxicity is thus compatible with their medical use as a drug.

The compounds of the present invention can selectively mimic or inhibit the effects of vasopressin and/or oxytocin. Among these compounds are antagonists for vasopressin receptors which can intervene in the regulation of the central and peripheral circulation, in particular coronary, renal and gastric circulation, and in hydric regulation and the liberation of adrenocorticotrophic hormone (ACTH). The vasopressin agonists can advantageously replace vasopressin or its analogues in the treatment of insipid diabetes they can also be used to treat enuresia, and in the regulation of hemostasis: the treatment of hemophilia, Von Willebrand's syndrome, an antidote for platelet aggregants, Laszlo F. A., Pharmacol. Rev., 1991, 43, 73–108. Drug Investigation, 1990, 2 (suppl. 5), 1–47. The hormones themselves, vasopressin and oxytocin, and certain of their peptide or non peptide analogues have been used therapeutically and their efficacy has been demonstrated (Vasopressin. Gross P. et al., ed. John Libbey Eurotext, 1993, in particular 243–257 and 549–562. Laszlo F. A. and Laszlo F. A. Jr., Clinical perspectives for vasopressin antagonists, Drug News Perspect., 1993, 6 (8); North W. G., J. Clin. Endocrinol., 1991, 73, 1316–1320. Legros J. J. et al., Prog. Neuro-Pharmacol. Biol. Psychiat., 1988, 12, 571–586; Andersson K. E. et al., Drugs Today, 1988, 24 (7), 509–528; Stump D. L. et al., Drugs, 1990, 39, 38–53; Caltabiano S. et al., Drugs Future, 1988, 13, 25–30; Mura Y. et al., Clin. Nephrol. 1993, 40, 60–61; Faseb J., 1994, 8 (5), A587: 3398).

V$_2$ antagonist molecules with an aquaretic profile exhibit a broad range of therapeutic indications and constitute a major innovation in the treatment of cardiac insufficiency, hyponatremia, hydric disorders, water retention, etc. This type of compound can advantageously replace conventional diuretics in all of the pathologies where they are recommended for man and animal. Such molecules can also be envisaged in the treatment of hypertension in combination with anti-hypertensors of other therapeutic classes such as beta blockers, conversion enzyme inhibitors or antagonists for angiotensin 11 receptors.

Thus the compounds of the invention can be used for the treatment of disorders of the central and peripheral nervous system, the cardiovascular system, the endocrine and hepatic system, the renal sphere, the gastric, intestinal and pulmonary sphere, in opthalmology and in sexual behaviour problems, in man and in animals.

The present invention thus also provides pharmaceutical compositions containing an effective dose of a compound according to the invention or a pharmaceutically acceptable salt, solvate or hydrate thereof, and suitable excipients.

Said excipients are selected depending on the pharmaceutical form and the desired mode of administration.

Pharmaceutical compositions of the present invention for oral, sublingual, subcutaneous, intramuscular, intravenous, topical, intra-tracheal, intra-nasal, transdermal, rectal or intraocular administration, the active principles with formula (I) above, or any salts, solvates or hydrates, can be administered in unitary administration forms, mixed with conventional pharmaceutical supports, to animals and to human beings prophylactically or to treat the above disorders or ailments. Suitable unitary administration forms comprise oral forms such as tablets, capsules, powders, granules and oral solutions or suspensions, sublingual, buccal, intratracheal, or intra-nasal, forms of administration, subcutaneous, intramuscular or intravenous administration forms, and rectal administration forms. For topical application, the compounds of the invention can be used in creams, ointments, lotions or eye lotions.

In order to obtain the desired prophylactic or therapeutic effect, the dose of active principle can vary in the range 0.01 to 50 mg per kg of body weight per day.

Each unitary dose can contain 0.5 mg to 1000 mg, preferably 1 mg to 500 mg, of active ingredients in combination with a pharmaceutical support. This unitary dose can be administered 1 to 5 times a day so as to administer a daily dose of 0.5 mg to 5000 mg, preferably 1 mg to 250 mg.

When a solid composition is prepared in the form of tablets, the principal active ingredient is mixed with a pharmaceutical vehicle, such as gelatine, starch, lactose, magnesium stearate, talc, gum arabic or the like. The tablets may be coated with saccharose, a cellulose derivative, or other suitable materials or they may be treated to endow them with a prolonged or retarded activity and so that they continuously release a predetermined quantity of active principle.

A capsule preparation is obtained by mixing the active ingredient with a diluant and pouring the mixture obtained into soft or hard capsules.

A preparation in the form of a syrup or elixir, or in the form of drops, may contain the active ingredient along with a sweetener, preferably calorie-free, methylparaben or propylparaben as an antiseptic, and with agents producing an appropriate flavour and colour.

Water-dispersible powders or granules can contain the active ingredient mixed with dispersing agents or with wetting agents, or with suspending agents such as polyvinylpyrrolidone, as well as with sweeteners or flavour correctors. For rectal administration, suppositories are used which are prepared with binders which melt at the rectal temperature, for example cocoa butter or polyethylene glycols.

For parenteral administration, aqueous suspensions, isotonic saline solutions or sterile and injectable solutions which contain pharmacologically acceptable dispersion and/or wetting agents, for example propylene glycol or butylene glycol are used.

The active principle can also be formulated in the form of microcapsules, optionally with one or more supports or additives, or with matrices such as a polymer or a cyclodextrin (patch, slow release forms).

The compositions of the invention can be used for the treatment or prevention of different vasopressin-dependent or oxytocin-dependent disorders and dysfunctions in the secretion of vasopressin or oxytocin, for cardiovascular disorders, such as hypertension, pulmonary hypertension, cardiac insufficiency, circulatory insufficiency, myocardial infarctus, atherosclerosis or coronary vasospasm, in particular in the smoker, unstable angina and PTCA (percutaneous transluminal coronary angioplasty), cardiac ischemia, disorders in haemostasis, in particular haemophilia, Von Willebrand's syndrome; disorders of the central nervous system, migraine, cerebral vasospasm, cerebral hemorrhagia, cerebral oedemas, depression, anxiety, bulimia, psychotic states, for example memory problems; renopathies and renal dysfunctions such as oedemas, renal vasospasm, necrosis of the renal cortex, nephrotic syndrome, hyponatremia, hypokalemia, diabetes, Schwartz-Bartter syndrome or renal lithiasis; disorders of the gastric system, such as gastric vasospasm, portal hypertension, hepatocirrhosis, ulcers, vomiting, for example nausea including nausea due to chemotherapy, travel sickness, or the syndrome of inappropriate anti-diuretic hormone (SIADH), insipid diabetes and enuresia; disorders of the hepatic system such as cirrhosis of the liver; abdominal ascites and all disorders causing abnormal water retention; adrenal disorders (Cushing's disease), in particular hypercorticism and hyperaldosteronemia, a variety of pancreatic disorders and the regulation of lipid metabolism in particular with oxytocin antagonists. The compositions of the invention can also be used for the treatment of sexual behavioural disorders, for over weight or excess weight and obesity advantageously replacing conventional diuretics already used for this indication. In women, the compositions of the invention can be used to treat dysmenorrhea or premature labour. The compositions of the invention can also be used in the treatment of small cell pulmonary cancer, hyponatremic encephalopathy, Raynaud's disease, Meniere's syndrome, pulmonary syndrome, glaucoma and the prevention of cataracts and in postoperative treatments, in particular after abdominal, cardiac or hemorragic surgery.

In addition to the products with formula (I) above or their pharmaceutically acceptable salts, solvates or hydrates, the compositions of the present invention can contain other active principles which can be used in the treatment of the disorders or diseases indicated above.

Thus the present invention also provides pharmaceutical compositions containing a plurality of active principles in association, one of which is a compound of the invention.

Thus, in accordance with the present invention, pharmaceutical compositions can be prepared containing a compound of the invention associated with a compound acting on the renin-angiotensin system such as a conversion enzyme inhibitor, an antagonist of angiotensine II, a renine inhibitor. A compound of the invention can also, for example, be associated with a peripheral vasodilator, a calcic inhibitor, a beta-blocker, an alpha-1-blocker or a diuretic. Such compositions will be of particular use in the treatment of hypertension or heart failure. Two compounds of the invention can also be combined: a specific antagonist for the V1 receptor with a specific oxytocin antagonist or a $V_1$ antagonist and a $V_2$ antagonist or a $V_2$ antagonist and a $V_1$ agonist.

Advantageously, the compositions of the present invention contain a product with formula (IA) above or one of its pharmaceutically acceptable salts, solvates or hydrates. Each of these compounds can also be associated with a specific antagonist of angiotensine II, preferably irbesartan.

These combinations can reinforce the therapeutic activities of the compounds of the invention.

The following PREPARATIONS and EXAMPLES illustrate the invention without in any way limiting its scope.

Unless otherwise indicated, the nuclear magnetic resonance spectra were produced in DMSO-d6, at 200 MHz and the chemical shifts are expressed in ppm.

The following abbreviations are used:

s=singlet m=multiplet t=triplet q=quadruplet
d=doublet

PREPARATION 1 Alcohols with Formula (IIIB)

5-Ethoxy-3-spiro-(4-hydroxycyclohexane)indolin-2-one. Compound (IIIB1)

A solution of 22 g of 5-ethoxy-3-spiro-(4-methoxy-methyloxycyclohexane) indolin-2-one prepared as described in EP 636 608 in 130 ml of methanol and 9 ml of concentrated hydrochloric acid (36%) is heated at 40° C. for 3 hours. The reaction mixture is cooled, then in succession the precipitate is drained, rinsed with diethyl ether and dried to obtain the polar isomer of the expected product: M.p.=225° C. 50 ml of water are added to the filtrate, then in succession the methanol is evaporated off, the reaction mixture is extracted with dichloromethane, the organic phases are washed with water, dried and evaporated off to obtain the expected product in the form of a mixture of isomers; M.p.=170° C.

5-Chloro-3-spiro-(4-hydroxycyclohexane)indolin-2-one. Compound (IIIB2)

The same operating procedure as above is carried out, starting from 5-chloro-3-spiro-(4-methoxymethyloxycyclohexane)indolin-2-one prepared from 5-chloroindolin-2-one using the method described in EP 636 608. After extracting with dichloromethane, the expected product is isolated in the form of a mixture of isomers: M.p.=260° C.

PREPARATION 2 Hydrazides with Formula (VI)

N'-(4-Ethoxyphenyl)-4,4-ethylenedioxycyclohexanecarbohydrazide. Compound (VI.1)

At −40° C., 1.65 ml of isobutyl chloroformate are added to a mixture of 2.63 g of sodium 4,4-ethylenedioxycyclohexanoate in 20 ml of tetrahydrofuran followed by 1.8 ml of triethylamine. The reaction mixture is stirred for 2 hours at 0° C., then at −20° C., 2.4 g of 4-ethoxyphenylhydrazine hydrochloride are added; the reaction mixture is stirred for 2 hours at 0° C. then 100 ml of water are added and it is extracted with ethyl acetate. The organic phases are washed successively with water, with a solution of potassium bisulfate (pH=2), with a saturated potassium carbonate solution, dried over magnesium sulfate and evaporated off. The expected product is obtained after crystallisation from diethyl ether; M.p.=158° C.

N'-Phenyl-4,4-ethylenedioxycyclohexanecarbohydrazide. Compound (VI.2)

Compound (VI.2) is isolated from phenylhydrazine in the same manner;

M.p.=158° C.

PREPARATION 3 Acetals with Formula (VB)

5-Ethoxy-3-spiro-(4,4-ethylenedioxycyclohexane)indolin-2-one. Compound (VB1)

At −50° C., 2.15 ml of a solution of 1.6M butyllithium in hexane are added to a suspension of 1 g of hydrazide (VI.1) in 16 ml of tetrahydrofuran. The reaction mixture is stirred for 15 minutes and 16 ml of tetraline are added. The tetrahydrofuran is distilled off, and the mixture is heated to 180° C. for 45 minutes. 20 ml of ethyl acetate are then added at room temperature, then in succession, the reaction mixture is washed with water, the organic phase is dried over magnesium sulfate, the solvents are distilled off under vacuum and the residue is chromatographed on silica gel while eluting with a 7/3 cyclohexane/ethyl acetate (v/v) mixture. The expected product is isolated by crystallisation from diethyl ether; M.p.=183° C. The same product is also obtained by reacting 5-ethoxy-3-spiro-(4-oxocyclohexane) indolin-2-one (compound (IIB1)) with ethylene glycol in cyclohexane in the presence of a 5 A molecular sieve and paratoluenesulfonic acid in catalytic quantities.

5-Ethoxy-3-spiro-(4,4-propylenedioxycyclohexane)indolin-2-one. Compound (VB2)

The same operating procedure as described above to prepare compound (VB1) is carried out starting from the corresponding hydrazide or by reacting 5-ethoxy-3-spiro-(4-oxocyclohexane)indolin-2-one (compound (IIB1)) with 1.3-propane-diol in cyclohexane in the presence of a 5 Å molecular sieve and paratoluenesulfonic acid in catalytic quantities; M.p.=216° C.

3-Spiro-(4,4-ethylenedioxycyclohexane)indolin-2-one. Compound (VB3)

The operating procedure described above for the preparation of compound (V1) is carried out, starting from the corresponding hydrazide (VI.1); M.p.=218° C.

PREPARATION 4 Ketones with Formula (IIB)

5-Ethoxy-3-spiro-(4-oxocyclohexane)indolin-2-one. Compound (IIB1)

3.8 g of 5-ethoxy-3-spiro-(4-hydroxycyclohexane) indolin-2-one (IIIB1) (mixture of isomers) and 5.8 ml of pyridine are dissolved in 250 ml of ethyl acetate and 6.3 g of pyridinium chlorochromate adsorbed on 29 g of neutral alumina are added. The reaction mixture is then stirred at 25° C. for 16 hours, it is then filtered and the solvent is evaporated from the filtrate. 3.4 g of the expected product are isolated after recrystallisation in the presence of activated carbon in toluene; M.p.=168° C.

The same product is prepared by hydrochloric hydrolysis of compound VB1.

5-Chloro-3-spiro-(4-oxocyclohexane)indolin-2-one. Compound (IIB2)

This compound is prepared using the same operating procedure as that used to prepare compound (IIB1) from 5-chloro-3-spiro-(4-hydroxycyclo-hexane)indolin-2-one (IIIB2); M.p.=220° C.

PREPARATION 5 Reactants with formula (2)

2-methoxy-4-N-tert-amylcarbamoylbenzenesulfonyle chloride. Reactant (2).1 a) N-tert-amyl(3-methoxy-4-nitro)benzamide

At 10° C., 30 ml of tert-amylamine are added to a solution of 27 g of 3-methoxy-4-nitrobenzoyl chloride (obtained from 25 g of the corresponding acid and thionyl chloride refluxed for 4 hours followed by vacuum evaporation) in 250 ml of dichloromethane. The reaction mixture is stirred for 30 minutes at 20° C., then 100 ml of a 1N hydrochloric acid solution are added, it is decanted, washed and the organic phase is dried over magnesium sulfate, then the solvent is evaporated off and the residue is chromatographed on silica gel, while eluting with dichloromethane to obtain 31 g of the expected product; M.p.=65° C.

Similarly, N-tert-butyl(3-methoxy-4-nitro)benzamide is prepared from N-tert-butylamine; M.p.=1180C.

b) N-tert-amyl-(3-methoxy-4-amino)benzamide

A mixture of 31 g of N-tert-amyl-(3-methoxy-4-nitro) benzamide obtained in a), 20 g of 10% palladium on carbon, 76 ml of cyclohexene in 310 ml of ethanol is refluxed for 3 hours. It is filtered, and the filtrate is evaporated off to obtain 25 g of the expected product; M.p.=160° C.

c) 2-methoxy-4-tert-amylcarbamoylbenzenesulfonyl chloride

A solution of 7.9 g of sodium nitrite in 31 ml of water is added to a solution of 25 g of N-tert-amyl-(3-methoxy-4-amino)benzamide in 103 ml of acetic acid and 187 ml of 36% hydrochloric acid at 0° C. The reaction mixture is stirred for 1 hour at 0° C. then this solution, kept at 0° C., is added to a suspension of 6.8 g of cupric chloride in 25 ml of water and 140 ml of acetic acid saturated at 0° C. with about 69 g of sulfur dioxide. The reaction mixture is stirred at 0° C. for 3 hours then at 20° C. for 16 hours and the mixture is poured onto 750 g of ice then stirred for 1 hour at 20° C. It is dried, then in succession, the precipitate is rinsed with water and dried under vacuum for 48 hours to obtain 19 g of the expected product; M.p.=104° C.
4-N-tert-butylcarbamoyl-2-methoxybenzenesulfonyl chloride. Reactant (2).2

The expected reactant is isolated from N-tert-butyl(3-methoxy-4-amino)benzamide in the same manner; M.p.= 148° C.
2-methoxy-4-benzyloxycarbonylbenzenesulfonyl chloride. Reactant (2).3

Using the same reaction as above, and starting from the benzyl ester of 4-amino-3-methoxybenzoic acid (M.p.=72° C., obtained from reducing the corresponding nitrated derivative using tin in a hydrochloric medium M.p.=88° C.), the expected reactant is isolated; M.p.=55° C.
N-tert-butyl-4-bromomethyl-3-methoxybenzamide. Reactant (2).4

A mixture of 3 g of N-tert-butyl-4-methyl-3-methoxybenzamide, 2.4 g of N-bromosuccinimide, 0.16 g of benzoyl peroxide in 40 ml of carbon tetrachloride is stirred at 30° C., under irradiation with visible light for 48 hours. The solvent is evaporated off, then in succession 25 ml of water is added, the mixture is extracted with diethyl ether, dried over magnesium sulfate, the solvent is evaporated off and the residue is chromatographed on silica gel, eluting with an 8/2 cyclohexane/ethyl acetate (v/v) mixture. The expected reactant is isolated after crystallisation from isopropyl ether; M.p.=114° C.

PREPARATION 6 Protected alcohols with formula (IVA)

5-Ethoxy-3-spiro-(4-methoxymethyloxycyclohexane)-1-[(4-N-tert-butylcarbamoyl-2-methoxybenzenesulfonyl] indolin-2-one. Compound (IVA1)

0.283 g of potassium tert-butoxide is added to a solution, cooled to −40° C., of 5-ethoxy-3-spiro-(4-methoxymethyloxycyclohexane)indolin-2-one, (compound with formula (IVB)) prepared as described in EP 636 608, in 80 ml of tetrahydrofuran. The temperature is allowed to rise to 0° C. then the mixture is cooled to −40° C. and 0.73 g of (2-methoxy-4-N-tert-butylcarbamoyl) benzenesulfonyl chloride in 7 ml of tetrahydrofuran is added. The reaction mixture is stirred for 2 hours at room temperature, then in succession, 20 ml of water are added, the mixture is extracted with ethyl acetate, dried over magnesium sulfate, the solvent is evaporated off and the oil obtained is purified by silica gel chromatography, while eluting with an 8/2 cyclohexane/ethyl acetate (v/v) mixture. The least polar isomer of the expected product is isolated; M.p.=165° C., then the polar isomer; M.p.=156° C.

PREPARATION 7 Alcohols with Formula (IIIA)
5-Ethoxy-3-spiro-(4-hydroxycyclohexane)-1-[(4-N-tert-butylcarbamoyl-2-methoxybenzenesulfonyl]indolin-2-one. Compound (IIA1)

A mixture of the polar isomer of compound (IVAL) in 1.2 ml of methanol and 0.24 ml of concentrated hydrochloric acid (36%) is heated at 50° C. for 1 hour. 8 ml of water are added to the reaction mixture, then in succession, the mixture is extracted with dichloromethane, the organic phases are dried over magnesium sulfate and the solvents are evaporated off. The expected product is obtained after purification by silica gel chromatography, while eluting with dichloromethane; M.p.=268° C. (polar isomer).

Similarly, from the least polar isomer prepared as described for (IVA1), the least polar isomer of the expected product is isolated; M.p.=130° C. (hemihydrate). Compound (IIIA2).

PREPARATION 8 Ketones with formula (IIA)
5-Ethoxy-3-spiro-(4-oxocyclohexane)-1-[4-(4-N-tert-butylcarbamoyl)-2-methoxybenzenesulfonyl]indolin-2-one. Compound (IIA1)

At −40° C., 0.38 g of potassium tert-butoxide is added to a solution of 0.8 g of 5-ethoxy-3-spiro-(4-oxocyclohexane) indolin-2-one (compound (IIB1)) in 15 ml of tetrahydrofuran and the reaction mixture is stirred for 15 minutes at 0° C. At −40° C., 0.98 g 2-methoxy-4-(4-N-tert-butylcarbamoyl) benzene-sulfonyl chloride dissolved in 10 ml of tetrahydrofuran is added and the reaction mixture is stirred at 20° C. for 8 hours. 30 ml of water are added, the solvent is evaporated off under reduced pressure, extracted with dichloromethane, dried over magnesium sulfate and the solvent is evaporated off under reduced pressure. The expected product is isolated after purification by silica gel chromatography, while eluting with a 8/2 cyclohexane/ethyl acetate (v/v) mixture and recrystallisation from a 3/7 cyclohexane/ethyl acetate (v/v) mixture; M.p.=120° C. the same compound was also obtained by oxidising compound (IIIAL) under the conditions described in PREPARATION 4.

In the same manner, the following are isolated from the corresponding sulfonyl chlorides and indolin-2-ones:
5-Ethoxy-3-spiro-(4-oxocyclohexane)-1-[4-(4-N-tert-amylcarbamoyl)-2-methoxybenzenesulfonyl]indolin-2-one.Compound (IIA2); M.p.=191° C.
5-Chloro-3-spiro-(4-oxocyclohexane)-1-[4-(4-N-tert-butylcarbamoyl)-2-methoxybenzenesulfonyl]indolin-2-one hemihydrate. Compound (IIA3); M.p.=262° C.

PREPARATION 9 Indolin-2-one with formula (II'B)
5-Ethoxy-3-spiro-[4-(2-formylethylidene)cyclohexane] indolin-2-one. Compound (II'B1)

(II'B1): $R_1$=OC$_2$H$_5$; $R_2$=H; $R_3$=2-OCH$_3$;
Y'$_1$+Y'$_2$=CHCH$_2$CHO 24 ml of a 1M solution of sodium bistrimethylsilylamide in tetrahydrofuran are added at 0° C. to a solution of 6 g of (3,3-diisopropyloxy)-propyl triphenylphosphonium bromide (prepared as described in Synthesis, 1988, 395) in 100 ml of tetrahydrofuran. The reaction mixture is stirred for one and a half hours then 2.1 g of compound (IIB2) in 20 ml of tetrahydrofuran are added at −60° C. and the mixture is stirred for 12 hours at 20° C. The solvent is evaporated off, the diisopropylacetal of the expected product is isolated by silica gel column chromatography, while eluting with a 25/75 ethyl acetate/cyclohexane (v/v) mixture followed by hydrolysis for 2 hours at 20° C. in a mixture of 3.5 ml of dimethylketone, 3.5 ml of water and 0.02 ml of concentrated hydrochloric acid. The mixture is extracted with ethyl acetate, the organic phase is washed with a saturated solution of sodium bicarbonate, dried over sodium sulfate and the expected product is isolated after evaporating off the solvent.

$^1$H NMR=10.1 (s, 1H); 9.6 (s, 1H); 6.95 (s, 1H); 6.7 (s, 2H); 5.35 (t, 1H); 4 (q, 2H); 3.2 (d, 2H); 2.6 (m, 2H); 2.3 (m, 2H); 1.65 (m, 4H); 1.25 (t, 3H);
5-Ethoxy-3-spiro-(4-cyanocyclohexane)indolin-2-one Compound (II'B2)

0.2 g of tosylmethylisonitrile and 0.32 g of potassium tert-butoxide are added at −10° C. to a suspension of 0.25 g of 5-ethoxy-3-spiro-(4-oxocyclo-hexane)indolin-2-one in 5 ml of 1,2-dimethyloxyethane and 1 ml of ethanol. The mixture is stirred at 15° C. for 3 hours, 5 ml of a saturated ammonium chloride solution was added, extracted with ethyl acetate, dried over sodium sulfate and the solvent is evaporated off under reduced pressure. The expected product (mixture of isomers) is isolated after silica gel column chromatography, while eluting with a mixture of 98/2 dichloromethane/methanol (v/v) and recrystallising from toluene; M.p.=174° C.

5-Chloro-3-spiro-(4-cyanocyclohexane)indolin-2-one. Compound (II'B3)

0.86 g of tosylmethylisonitrile then 1.35 g of potassium tert-butoxide are added at 16° C. to a solution of 1 g of compound (IIB2) in 20 ml of dimethylsulfoxide. The mixture is stirred for 2 hours at 20° C. then 40 ml of an aqueous 5% ammonium chloride solution are added, the mixture is extracted with dichloromethane, dried over sodium sulfate and the solvent is evaporated off under reduced pressure. The residue is chromatographed on a silica gel column while eluting with dichloromethane, taken up into diethyl ether, and dried at 50° C. under reduced pressure. The expected product is then isolated (mixture of isomers): M.p.=186° C.

5-Chloro-3-spiro-[4-(2-aminoethyl)cyclohexane]indolin-2-one. Compound (II'B4)

a) 5-Chloro-3-spiro-(4-cyanomethylidene-cyclohexane) indolin-2-one isomer A

5-Chloro-3-spiro-(4-cyanomethylcyclohex-3-ene) indolin-2-one isomer B as described in Synthesis, 1977, 629

0.4 g of powdered potassium hydroxide is added to 0.7 g of compound (IIB2) in 10.5 ml of acetonitrile, in an inert atmosphere at 10° C. The mixture is heated slowly to a temperature of 80° C. then cooled before adding 20 ml of 0.5N hydrochloric acid then 80 ml of ethyl acetate. The organic phase is dried over sodium sulfate, evaporated to dryness, chromatographed on a silica gel column while eluting with a 90/10 cyclohexane/ethyl acetate (v/v) mixture. Two isomers are isolated:

compound A: the least polar; M.p.=78° C.;
compound B: the most polar; M.p.=155° C.

b) 5-Chloro-3-spiro-[4-(2-aminoethyl)-cyclohexane]indolin-2-one 0.14 g of compound A and 0.11 g of compound B in 50 ml of a 10% solution of ammonia in methanol are hydrogenated at a pressure of 2 MPa of hydrogen for 24 hours at 32° C. in the presence of 0.30 g of moist Raney nickel. The mixture is cooled to 10° C., the catalyst is filtered, and the solvents are evaporated off to obtain the expected product in the form of a mixture of two isomers; M.p.=90° C.

PREPARATION 10 Compounds with Formula
(II'A)

5-Chloro-1-[4-N-tert-butylcarbamoyl-2-methoxybenzenesulfonyl]-3-spiro-[4-(methoxymethylidene)cyclohexane]indolin-2-one. Compound (II'A1)

The method described in J. Am. Chem. Soc., 1967, 89, 1492 is used.

0.66 g of (methoxymethyl)triphenylphosphonium chloride are added at 0° C. to a solution of lithium diisopropylamide (prepared at 4° C. by adding 0.6 ml of a solution of 1.6M of butyllithium in hexane to 0.13 ml of diisopropylamine in 4 ml of diethyl ether), and the reaction mixture is stirred for 30 minutes. It is cooled to −30° C., 0.250 g of compound (IIA3) in 4 ml of tetrahydrofuran is added, the reaction mixture is stirred for 8 hours at 10° C., hydrolysed and extracted with diethyl acetate. The organic phase is washed with a saturated sodium chloride solution, dried over magnesium sulfate, the solvents are evaporated off under reduced pressure and the expected product is isolated by silica gel column chromatography, while eluting with an 85/15 cyclohexane/ethyl acetate (v/v) mixture; M.p.=180° C.

5-Chloro-1-[4-N-tert-butylcarbamoyl)-2-methoxybenzenesulfonyl]-3-spiro-[4-formylcyclohexane] indolin-2-one. Compound (II'A2)

A mixture of 0.12 g of compound (II'A1) in 4 ml of tetrahydrofuran and 1 ml of an aqueous 30% perchloric acid solution is stirred at 20° C. for one hour. 20 g of ice are added, it was extracted with ethyl acetate, dried over sodium sulfate and the expected product was isolated after evaporating off the solvents under reduced pressure; M.p.=198° C.

PREPARATION 11 Compounds with formula
(II"B)

5-Ethoxy-3-spiro-[4-(2-morpholinoethylthio)cyclohex-3-ene]indolin-2-onle. Compound (II"B1)

a) 2-morpholinoethanethiol was synthesised using the method described in JACS, 1948, 70, 950.

b) 5-Ethoxy-3-spiro-[4-(2-morpholinoethylthio)cyclohex-3-ene]indolin-2-one

At −10° C., 1.13 g of 2-morpholinoethanethiol then 0.6 ml of trifluoroborane etherate are added to a solution of 0.5 g of 5-ethoxy-3-spiro-(4-oxocyclohexane) indolin-2-one (Compound IIB1) in 20 ml of dichloromethane. The reaction mixture is heated for 5 hours under reflux. At 10° C., 10 ml of an aqueous 5% $K_2CO_3$ solution is added then the mixture is extracted with dichloromethane. It is decanted, dried over $Na_2SO_4$, the solvent is evaporated off. The residue obtained is chromatographed on a silica gel column while eluting with a 98/2 dichloromethane/methanol (v/v) mixture to provide the expected product.

$^1$H NMR=6.7 (s, 2H); 6.55 (s, 1H); 5.7 (m, 1H); 3.9 (q, 2H); 3.55 (t, 4H); 2.85 (m, 2H); 2.5 (m, 2H); 2.35 (m, 6H); 2.1–1.8 (m, 2H); 1.55 (m, 1 H); 1.23 (t, 3H); 1.24 (m,1 H).

PREPARATION 12 Indolin-2-ones with formula
(I')

5-Ethoxy-3-spiro-[4-(3-morpholinopropylidene) cyclohexane]indolin-2-one. Compound (I'1)

(I'1): $R_1=OC_2H_5$; $R_2=H$;

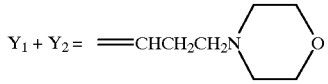

0.23 ml of morpholine, 0.42 g of sodium triacetoxyborohydride, and 0.075 ml of acetic acid are added to 0.4 g of compound (II'B1) in 10 ml of tetrahydrofuran, and the reaction mixture is stirred for 20 hours at 20° C. 10 ml of 1N hydrochloric acid are added and the aqueous phase is extracted with diethyl ether. The organic phase is removed. The aqueous phase is alkalinised with 10N sodium hydroxide, extracted with ethyl ether and dried over sodium sulfate. The expected product is isolated after evaporating off the solvent under reduced pressure.

$^1$H NMR=10.1 (s, 1H); 6.95 (s, 1H); 6.7 (s, 2H); 5.2 (t, 1H); 3.9 (q, 2H); 3.5 (m, 4H); 2.6–2.2 (m, 12H); 1.6 (m, 4H); 1.25 (t, 3H).

5-Ethoxy-3-spiro-[4-(3-morpholinopropyl)cyclohexane] indolin-2-one. Compound (I'2)

(I'2): $R_1=OC_2H_5$; $R_2=H$;

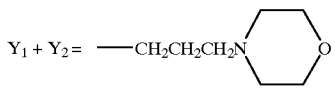

0.44 g of compound (I'1) in 25 ml of ethanol is hydrogenated at 1.5 MPa at 40° C. for 24 hours in the presence of 0.2 g of 10% palladium on carbon. The catalyst is separated out by filtering, the solvent is evaporated off and the expected product (mixture of isomers) is isolated by silica gel column chromatography, while eluting with a 98.5/1.5 dichloromethane/methanol (v/v) mixture.

$^1$H NMR=10.1 (s, 0.3H); 9.95 (s, 0.7H); 7 (s, 0.3H); 6.84 (s, 0.7H); 6.75–6.65 (m, 2H); 3.9 (t, 2H); 3.5 (t, 4H); 2.3 (m, 6H); 1.8–1.15 (m, 16H);

5-Ethoxy-3-spiro-[4-(2-morpholinoethylthio)cyclohexane]indolin-2-one. Compound (I'3)

(I'3): $R_1=OC_2H_5$; $R_2=H$;

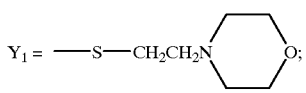

$Y_2=H$ 0.11 g of 5-ethoxy-3-spiro-[4-(2-morpholinoethylthio) cyclohex-3-ene]indolin-2-one (Compound II"B1) in 20 ml of ethyl acetate is hydrogenated at 2 MPa at 55° C. for 20 hours in the presence of 0.1 g of 5% palladium on carbon. The catalyst is separated by filtering, the solvent is evaporated off and the expected product is isolated which crystallizes out: M.p.=105° C.

5-Chloro-3-spiro-[4-spiro-(S-dihydro-3H-furan-2-one) cyclohexane]indolin-2-one.

Compound (I'4) prepared as described in J. Chem. Soc., Chem. Commun. 1986, 624–625.

(I'4): $R_1=5$-Cl; $R_2=H$;

48 ml of a solution of 0.1M samarium (II) iodide in tetrahydrofuran are added at 0° C. to 0.4 g of compound (IIB2) in 0.17 ml of tert-butanol and 0.16 ml of methyl acrylate. The reaction mixture is stirred at 3° C. for 1 hour then 100 ml of 0.5N HCl are added. The mixture is extracted with ethyl acetate, the organic phase is washed with an aqueous sodium bisulfite solution, dried over sodium sulfate and evaporated under reduced pressure. The expected product is isolated by silica gel column chromatography, while eluting with dichloromethane; M.p.=274° C.

5-Chloro-3-spiro-{[4-hydroxy-4-(2-N-(2-carboxamidoethyl)carbamoyl)ethyl]cyclohexane}indolin-2-one. Compound (I'5)

(I'5): $R_1=5$-Cl; $R_2=H$; $Y_1=(CH_2)_2CONH(CH_2)_2CONH_2$; $Y_2=OH$ 0.4 g of compound (I'4), 0.2 g of beta-alanine amide base and 3 ml of ethanol were stirred in an autoclave at 107° C. for 3 days. The solvent is evaporated off, chromatography on a silica gel column and eluted with a dichloromethane/methanol solution varying from 100/0 to 90/10 is carried out to isolate the expected product; M.p.=134° C.

5-Chloro-3-spiro-[4-(2-tert-butoxycarbonylaminoethyl) cyclohexane]indolin-2-one. Compounds (I'6) and (I'7)

(I'6) and (I'7): $R_1=5$-Cl; $R_2=H$; $Y_1=$—$(CH_2)_2NHCOOC(CH_3)_3$; $Y_{2=H}$ 0.26 g of di-tert-butyldicarbonate and 0.05 g of magnesium oxide are added to 0.25 g of compound (II'B4) in 5 ml of dioxane and 0.5 ml of 2N sodium hydroxide. The reaction mixture is stirred at 20° C. for 16 hours then 20 ml of water are added and extracted with ethyl acetate. The organic phase is dried over sodium sulfate, the solvents are evaporated off, then chromatography is carried out on a silica gel column while eluting with dichloromethane. The product was isolated in the form of 2 isomers compound (I'6): the least polar; M.p.=85° C.

compound (I'7): the more polar; M.p.=78° C.

5-Chloro-3-spiro-[(4-tert-butoxycarbonylaminomethyl) cyclohexane]indolin-2-one. Compound (I'8)

(I'8): $R_1=5$-Cl; $R_2=H$; $Y_1=CH_2NHCOOC(CH_3)_3$; $Y_2=H$ 0.21 g of compound (II'B3) in 20 ml of 14% ammoniacal solution in methanol is hydrogenated under 2.5 MPa of hydrogen for 48 hours at 28° C. in the presence of 0.5 g of moist Raney nickel. At 15° C., the catalyst is eliminated by filtering, the filtrate is evaporated off, the residue is taken up in 5 ml of 1,4-dioxane, 0.5 ml of water, treated with 0.34 ml of 2N sodium hydroxide, 0.04 g of magnesium oxide and 0.17 g of di-tert-butyidicarbonate. The reaction mixture is stirred at 20° C. for 3 hours, 10 ml of water are added and it is extracted with ethyl acetate. The organic phase is dried over sodium sulfate, evaporated under reduced pressure and the expected product is isolated (mixture of isomers) by silica gel column chromatography, while eluting with a 99/1 dichloromethane/methanol (v/v) mixture; M.p.=86° C.

PREPARATION 13 Amine-containing reactants with Formula (1)

2-(4-Benzyloxypiperidino)ethylamine

1) N-(2-(4-Benzyloxypiperidino)ethyl)phthalimide

A mixture of 4.5 g of N-(2-bromoethyl)phthalimide, 3.2 g of 4-benzyl-oxypiperidine and 4.5 g of potassium carbonate in 40 ml of acetonitrile is heated to 55° C. for 8 hours. It is filtered, the filtrate is extracted with ethyl acetate, the organic phase is washed three times with 50 ml of water, dried over magnesium sulfate and the solvent is evaporated off under reduced pressure. The expected compound isolated in the form of an oil is used as is in the following step.

2) 2-(4-Benzyloxypiperidino)ethylamine

The preceding compound and 2.5 ml of hydrazine hydrate are refluxed in 100 ml of methanol for 3 hours. The reaction mixture is cooled to 50° C., filtered and the filtrate is concentrated under reduced pressure. 25 ml of 6N hydrochloric acid are added and the mixture is heated to 50° C. for 1 hour. It is cooled to 0° C., filtered and the filtrate was alkalinised with concentrated sodium hydroxide. The reaction mixture is extracted with dichloromethane, dried over anhydrous sodium sulfate and the solvent is evaporated off under reduced pressure. The expected product was isolated by vacuum distillation.

B.p.=105–110° C. at 4 Pa.

6-amino hexanoic acid amide:

Prepared as described in JACS, 1946, 68, 1684 and Chem. Ber. 1959, 92, 2616–2620.

EXAMPLE 1

5-Ethoxy-1-[4-(N',N'-diethylureido)-2-methoxybenzenesulfonyl]-3-spiro-(4-morpholinocyclohexane)indolin-2-one (I): $R_1=OC_2H_5$; $R_2=H$; $R_3=2$-$OCH_3$; $W=SO_2$; $R_4=4$-$NHCON(C_2H_5)_2$;

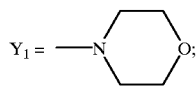

$Y_2$=H 0.150 g of sodium triacetoxyborohydride and 0.03 g of acetic acid are added to a solution of 0.25 g of 5-ethoxy-1-[4-(N',N'-diethylureido)-2-methoxybenzenesulfonyl]-3-spiro-[4-oxocyclohexane)indolin-2-one (prepared as described in EP 636 608) in 2.5 ml of 1,2-dichloroethane and 0.04 g of morpholine, at 20° C. The reaction mixture is stirred for 16 hours at 20° C., then 4 ml of a saturated sodium bicarbonate solution are added and it is extracted with ethyl acetate. It is dried over magnesium sulfate, the solvent is evaporated off under reduced pressure and a mixture of isomers of the expected product is obtained which is purified by chromatography on a silica gel column while eluting with cyclohexane then with a 98/2 dichloromethane/methanol (v/v) mixture. The least polar isomer of the expected product is isolated. (Thin layer chromatography, silica, elution with 93/7 dichloromethane/methanol (v/v), Rf=0.55); M.p.=105° C., then the polar isomer (Rf=0.46); M.p.=125° C.

In the same manner, by changing the ketones (IIA) and the amines, the compounds of EXAMPLES 2 to 13 shown in TABLE 1 below are obtained:

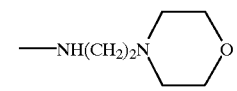

| Ex. N° | $R_1$ | $R_4$ | $Y_1$ | Salt, solvate (1) | M.p. ° C. |
|---|---|---|---|---|---|
| 2 | —OC$_2$H$_5$ | —NHCON(C$_2$H$_5$)$_2$ | —N(CH$_3$)$_2$ | 2 CH$_3$OH, 2 H$_2$O | 198 |
| 3 | —OC$_2$H$_5$ | —NHCON(C$_2$H$_5$)$_2$ | —NHCH$_3$ | CH$_3$COOC$_2$H$_5$ (2) | 120 |
| 4 | —OC$_2$H$_5$ | —NHCON(C$_2$H$_5$)$_2$ | —NHCH$_3$ | CH$_3$COOC$_2$H$_5$ 0.5 H$_2$O (3) | 112 |
| 5 | —OC$_2$H$_5$ | —CONHC(CH$_3$)$_2$C$_2$H$_5$ | —NHCH$_3$ | H$_2$O | 140 |
| 6 | —OC$_2$H$_5$ | —CONHC(CH$_3$)$_2$C$_2$H$_5$ | —NHCH$_3$ | H$_2$O | 159 |
| 7 | —OC$_2$H$_5$ | —CONHC(CH$_3$)$_3$ | —NH(CH$_2$)$_2$N(morpholine) | H$_2$O (3) | 111 |
| 8 | —OC$_2$H$_5$ | —CONHC(CH$_3$)$_3$ | —NH(CH$_2$)$_2$N(morpholine) | H$_2$O (2) | 111 |
| 9 | —OC$_2$H$_5$ | —CONHC(CH$_3$)$_3$ | —NH(CH$_2$)$_2$N(piperidine-4-OCH$_2$-phenyl) | 0.5 CH$_3$OH (3) | 80 |
| 10 | —Cl | —CONHC(CH$_3$)$_3$ | —N(CH$_3$)$_2$ | HCl H$_2$O 0.7 C$_4$H$_{10}$O (3) | 285 |
| 11 | —Cl | —CONHC(CH$_3$)$_3$ | —N(CH$_3$)$_2$ | H$_2$O (2) | 189 |
| 12 | —Cl | —CONHC(CH$_3$)$_3$ | —NHCH$_3$ | | 232 |
| 13 | —Cl | —CONHC(CH$_3$)$_3$ | —NH(CH$_2$)$_5$CONH$_2$ | 1 pentane | 134 |

-continued

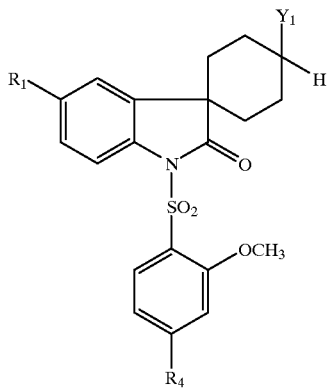

| Ex. N° | R₁ | R₄ | Y₁ | Salt, solvate (1) | M.p. ° C. |
|---|---|---|---|---|---|

(1) unless otherwise indicated, a mixture of isomers
(2) least polar isomer
(3) most polar isomer

EXAMPLE 14

5-Ethoxy-3-spiro-[4-(N-methyl-2 -(morpholinoethyl)amino)cyclohexane]-1-[(4-N-tert-butylcarbamoyl-2-methoxy)benzenesulfonyl]indolin-2-one.

(I): Ra=OC$_2$H$_5$; R$_2$=H; R$_3$=2-OCH$_3$; W=SO$_2$; R$_3$=4-CONHC(CH$_3$)$_3$;

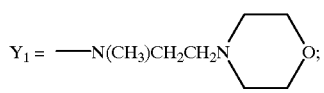

Y$_{2=H}$.

0.04 g of sodium cyanoborohydride and 0.046 ml of acetic acid are added to a solution, cooled to 5° C., of 0.13 g of the compound of EXAMPLE 7 in 1.3 ml of acetonitrile and 0.076 ml of an aqueous 37% formaldehyde solution. The reaction mixture is stirred for 3 hours at 20° C. and 2 ml of water, 2 ml of a saturated sodium bicarbonate solution are added and it is extracted with ethyl acetate. It is dried over anhydrous sodium sulfate and the solvent is evaporated off under reduced pressure. The pentahemihydrated dihydrochloride of the expected compound is isolated after purification on a silica gel column while eluting with a 97/3 dichloromethane/methanol (v/v) mixture and hydrochlorination in ethanol; M.p.=222° C.

EXAMPLE 15

5-Chloro-3-spiro-[4-(N-acetyl-5-carboxamidopentylamino)cyclohexane]-1-[(4-N-tert-butylcarbamoyl-2-methoxy)benzenesulfonyl]indolin-2-one.

(I): R$_1$=5-Cl; R$_2$=H; R$_3$=2-OCH$_3$; W=SO$_2$; R$_3$=4-CONHC(CH$_3$)$_3$; Y$_1$=—N(COCH$_3$)(CH$_2$)$_5$ CONH$_2$; Y$_2$=H.

0.014 g of acetyl chloride is added to 0.1 g of the compound of EXAMPLE 13 in solution in 2 ml of dichloromethane and 0.05 ml of triethylamine, at −30° C. At 20° C., 3 ml of water are added and the mixture is extracted with dichloromethane. The organic phase is dried over Na$_2$SO$_4$, the solvent is evaporated off, the residue is recrystallised from a 70/30 cyclohexane/ethyl acetate (v/v) mixture. It is filtered, dried at 20° C. under reduced pressure to obtain the expected product; M.p.=266° C.

EXAMPLE 16

5-Ethoxy-1-[4-(N',N'-diethylureido)-2-methoxybenzenesulfonyl]-3-spiro-[(4-hydroxy4-tert-butyloxycarbonylmethyl)cyclohexane]indolin-2-one.

(I): R$_1$=5-OC$_2$H$_5$; R$_2$=H; R$_3$=2-OCH$_3$; W=SO$_2$; R$_4$=4-NHCON(C$_{2H5}$)$_2$; Y$_1$=—CH$_2$COOC(CH$_3$)$_3$; Y$_2$=OH.

1.9 ml of a 1.6M butyllithium solution in hexane are added to 0.41 ml of diisopropylamine in 3 ml of tetrahydrofuran at −15° C. It is cooled to −70° C. and 0.2 g of tert-butyl acetate then 0.59 g of 5-ethoxy-1-[4-(N',N'-diethylureido)-2-methoxybenzenesulfonyl]-3-spiro-(4-oxo-cyclohexane) indolin-2-one (prepared as described in EP 636 608) are slowly added to the tetrahydrofuran mixture. The mixture is stirred at −60° C. for 40 minutes and 5 ml of a saturated aqueous ammonium chloride solution are added at that temperature. The mixture is extracted with ethyl acetate, dried over magnesium sulfate and the solvent is evaporated off under reduced pressure. The expected product in the form of a mixture of isomers is purified by chromatography on a silica gel column by successively eluting with dichloromethane then with a 99/1 dichloromethane/methanol mixture (v/v). The least polar isomer of the expected product is isolated (Thin layer chromatography, silica, eluting with 95/5 dichloromethane/methanol (v/v) (Rf=0.57); M.p.=135° C.; then the polar isomer (Rf=0.45); M.p.=140° C.

EXAMPLE 17

5-Ethoxy-1-[4-(N',N'-diethylureido)-2-methoxybenzenesulfonyl]-3-spiro-[(4-hydroxy-4-carboxymethyl)cyclohexane]indolin-2-one.

(I): W=SO$_2$; R$_4$=4-NHCON(C$_2$H$_5$)$_2$; Y$_1$=—CH$_2$COOH; Y$_2$=OH.

0.5 ml of trifluoroacetic acid is added to a solution of 0.05 g of the compound of EXAMPLE 16, and 0.2 ml of anisole in 0.8 ml of dichloromethane at −20° C. The reaction mixture is stirred at 20° C. for 5 hours and the solvents are evaporated under reduced pressure. The residue is taken up in 3 ml of water and extracted with ethyl acetate. It is dried over magnesium sulfate and the solvent is evaporated off under reduced pressure.

From the least polar isomer of EXAMPLE 16, the expected product, solvated with 1 mole of trifluoroacetic acid, is isolated; M.p.=145° C.

From the most polar isomer of the compound of EXAMPLE 16, the expected product, solvated with 1 mole of trifluoroacetic acid, is isolated M.p.=142° C.

EXAMPLE 18
5-Ethoxy-1-[(4-N-tert-butylcarbamoyl-2-methoxy) benzenesulfonyl]-3-spiro-(4-tert-butylcarboxymethylidenecyclohexane)indolin-2-one.

(I): $R_1$=5-$OC_2H_5$; $R_2$=H; $R_3$=2-$OCH_3$; W=$SO_2$; $R_3$=4-CONHC($CH_3$)$_3$; $Y_1$+$Y_2$=$=$CH—COOC($CH_3$)$_3$.

1.25 ml of tert-butyl-trimethylsilyl acetate then 2 g of compound (IIA1) in 20 ml of tetrahydrofuran are added to a solution, cooled to −70° C., of lithium diisopropylamide (prepared at 4° C. by adding 5.2 ml of 1.6N butyllithium in hexane to 1.15 ml of diisopropylamine in 15 ml of tetrahydrofuran). The reaction mixture is stirred for 30 minutes at −40° C. then 20 ml of an aqueous 3N hydrochloric acid solution is added. It is extracted with ethyl acetate, dried over magnesium sulfate and the solvents are evaporated off under reduced pressure. The expected product is isolated after chromatography on a silica gel column while eluting with an 80/20 cyclohexane/ethyl acetate mixture (v/v) M.p.=206° C.

EXAMPLE 19
5-Chloro-1-[(4-N-tert-butylcarbamoyl)-2-methoxy) benzenesulfonyl]-3-spiro-(4-tert-butylcarboxymethylidenecyclohexane)indolin-2-one.

(I): $R_1$=5-Cl; $R_2$=H; $R_3$=2-$OCH_3$; W=$SO_2$; $R_4$=4-CONHC($CH_3$)$_3$; $Y_1$+$Y_2$=$=$CH—COOC($CH_3$)$_3$.

Prepared as described in EXAMPLE 18 from compound (IIA3); M.p.=135° C.

EXAMPLE 20
5-Ethoxy-1-[(4-N-tert-butylcarbamoyl-2-methoxy) benzenesulfonyl]-3-spiro-(4-carboxymethylidenecyclohexane)indolin-2-one.

(I): $R_1$=5-$OC_2H_5$; $R_2$=H; $R_3$=2-$OCH_3$; W=$SO_2$; $R_4$=4-CONHC($CH_3$)$_3$; $Y_1$+$Y_2$=$=$CHCOOH.

14 ml of trifluoroacetic acid are added to a solution, cooled to −30° C., of 1.6 g of the compound of EXAMPLE 18 in 30 ml of dichloromethane, and stirred for 2 hours at 20° C. The reaction mixture is evaporated off under reduced pressure and the expected product is isolated by crystallisation from pentane (hydrate); M.p.=190° C.

EXAMPLE 21
5-Chloro-1-[(4-N-tert-butylcarbamoyl)-2-methoxy) benzenesulfonyl]-3-spiro-(4-carboxy-ethylidenecyclohexane)indolin-2-one.

(I): $R_1$=5-Cl; $R_2$=H $R_3$=2-$OCH_3$; W=$SO_2$; $R_4$=4-CONHC($CH_3$)$_3$. $Y_1$+Y=CHCOOH.

Prepared as described in EXAMPLE 20 from the compound of

EXAMPLE 19; M.p.=199° C.

EXAMPLE 22
5-Ethoxy-1-[(4-N-tert-butylcarbamoyl-2-methoxy) benzenesulfonyl]-3-spiro-(4-carboxymethylcyclohexane) indolin-2-one.

(I): $R_1$=5-$OC_2H_5$; $R_2$=H; $R_3$=2-$OCH_3$; W=S02; $R_4$=4-CONHC(H$_3$)$_3$; $Y_1$=—$CH_2$COOH; $Y_2$=H.

0.8 g of the compound of EXAMPLE 20 in 20 ml of acetic acid is hydrogenated at 1.5 MPa for 16 hours at 40° C. in the presence of 0.1 g of platinum oxide. The catalyst is separated by filtering, the filtrate is evaporated under reduced pressure and the expected product is isolated by crystallisation from pentane. (mixture of isomers); M.p.=192° C. ($H_2O$).

EXAMPLE 23
5-Ethoxy-1-[(4-N-tert-butylcarbamoyl-2-methoxy) benzenesulfonyl]-3-spiro-(4-morpholinocarbonylmethylidenecyclohexane)indolin-2-one.

(I): $R_1$=5-$OC_2H_5$; $R_2$=H; $R_3$=2-$OCH_3$; W=$SO_2$; $R_4$=4-CONHC($CH_3$)$_3$.

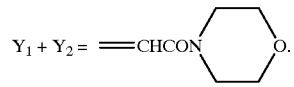

0.52 g of benzotriazole-1-yl-oxy-tris-(dimethylamino)-phosphonium hexafluorophosphate, 0.3 ml of triethylamine and 0.11 ml of morpholine are added to a suspension of 0.6 g of the compound of EXAMPLE 20 in 4 ml of acetonitrile at 5° C. The reaction mixture is stirred for 3 hours at 20° C. then the solvent is evaporated off under reduced pressure. The expected product is isolated by silica gel column chromatography, while eluting with a 99/1 dichloromethane/methanol (v/v) mixture and recrystallising from ethyl acetate; M.p.=238° C.

EXAMPLE 24
5-Ethoxy-1-[(4-N-tert-butylcarbamoyl-2-methoxy) benzenesulfonyl]-3-spiro-(4-(3-dimethylaminopropylaminocarbonylmethyl)cyclohexane) indolin-2-one.

(I): $R_1$=5-$OC_2H_5$; $R_2$=H; $R_3$=2-$OCH_3$; W=$SO_2$; $R_4$=4-CONHC($CH_3$)$_3$; $Y_1$=—$_{CH2}$CONH$_{(2)}$$_3$N($CH_3$)$_2$; $Y_2$=H.

Prepared as described in EXAMPLE 23 from the compound of EXAMPLE 22 and 3-dimethylaminopropylamine. (hydrate hydrochloride); M.p.=71° C.

EXAMPLE 25
5-Ethoxy-1-[(4-N-tert-butylcarbamoyl-2-methoxy) benzenesulfonyl]-3-spiro-(4-morpholinocarbonylmethylcyclohexane)indolin-2-one.

(I): $R_1$=5-$OC_2H_5$; $R_2$=H; $R_3$=2-$OCH_3$; W=$SO_2$; $R_4$=4-CONHC($CH_3$)$_3$;

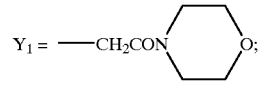

$Y_2$=H.

0.32 g of the compound of EXAMPLE 23 in 30 ml of ethanol is hydrogenated at 1.5 MPa for 16 hours at 40° C. in the presence of 0.3 g of 10% palladium on carbon. The catalyst is separated by filtering, the filtrate is evaporated off under reduced pressure and the hemihydrated expected product is isolated (mixture of isomers); M.p.=158° C.

The same compound is obtained by reacting the compound of EXAMPLE 22 with morpholine under the conditions described for EXAMPLE 23.

EXAMPLE 26
5-Chloro-1-[(4-N-tert-butylcarbamoyl-2-methoxy) benzenesulfonyl]-3-spiro-[4-N-(2-carboxamido-ethyl) carbamoylmethylidenecyclohexane]indolin-2-one.

(I): $R_1$=5-Cl; $R_2$=H; $R_3$=2-OCH$_3$; W=SO$_2$; $R_4$=4-CONHC(CH$_3$)$_3$; $Y_1$+$Y_2$==CH—CONH(CH$_2$)$_2$CONH$_2$.

Prepared as described in EXAMPLE 23 from the compound of EXAMPLE 21 and 3-aminopropanamide; M.p.=170° C.

EXAMPLE 27

5-Chloro-1-[(4-N-tert-butylcarbamoyl-2-methoxy)benzenesulfonyl]-3-spiro-[4-N-(4-N',N'-dimethylaminobutyl)carbamoylmethylidenecyclohexane]indolin-2-one.

(I): $R_1$=5-Cl; $R_2$=H; $R_3$=2-OCH$_3$; W=SO$_2$; $R_4$=4-CONHC(CH$_3$)$_3$; $Y_1$+$Y_2$==CH—CONH(CH$_2$)$_4$N(CH$_3$)$_2$.

Prepared as described in EXAMPLE 23 from the compound of EXAMPLE 21 and 4-dimethylaminobutylamine; M.p.=170° C. (H$_2$O).

EXAMPLE 28

5-Chloro-1-[(4-N-tert-butylcarbamoyl-2-methoxy)benzenesulfonyl]-3-spiro-[4-N-(4-N',N'-dimethylaminobutyl)carbamoylmethylcyclohexane]indolin-2-one.

(I): $R_1$=5-Cl; $R_2$=H; $R_3$=2-OCH$_3$; W=SO$_2$; $R_4$=4-CONHC(CH$_3$)$_3$; $Y_1$=—CH$_2$-CONH(CH$_2$)$_4$N(CH$_3$)$_2$; $Y_2$=H.

Prepared as described for EXAMPLE 25 from the compound of EXAMPLE 27; MP=273° C. (1HCl, 2C$_2$H$_5$OH).

EXAMPLE 29

5-Ethoxy-1-[4-(N-tert-butylcarbamoyl)-2-methoxybenzenesulfonyl]-3-spiro-[4-(3-morpholinopropyl)cyclohexane]indolin-2-one (Mixture of isomers).

(I): $R_1$=5-OC$_2$H$_5$; $R_2$=H; $R_3$=2-OCH$_3$; W=SO$_2$; $R_4$=4-CONHC(CH$_3$)$_3$;

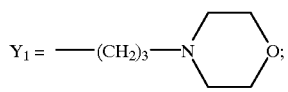

$Y_2$=H.

0.0374 g of potassium tert-butoxide is added to a solution of 0.113 g of compound (I'2) dissolved in 2 ml of tetrahydrofuran cooled to –40° C. and the temperature is allowed to rise to 0° C. 0.097 g of 4-(N-tert-butylcarbamoyl)-2-methoxybenzenesulfonyl chloride dissolved in 1 ml of tetrahydrofuran is added at –40° C. The reaction mixture is stirred for 3 hours at –20° C. then in succession, it is extracted with ethyl acetate, the organic phase is washed with a saturated ammonium chloride solution, dried over magnesium sulfate and the solvent is evaporated under reduced pressure. The base of the expected product is isolated by silica gel column chromatography, while eluting with a mixture of 99/1 dichloromethane/methanol (v/v) then the dihydrated hydrochloride is isolated by crystallisation from diethyl ether in the presence of hydrochloric acid; M.p.=184° C.

EXAMPLE 30

5-Ethoxy-1-[(4-(N-tert-butylcarbamoyl-2-methoxy)benzenesulfonyl]-3-spiro-[4-(2-morpholinoethylthio)cyclohexane]indolin-2-one.

(I): $R_1$=5-OC$_2$H$_5$; $R_2$=H; $R_3$2-OCH$_3$; W=SO$_2$; $R_4$=4-CONHC(CH$_3$)$_3$;

$Y_2$=H.

0.037 g of potassium tert-butoxide is added to a solution of 0.11 g of compound (I'3) in 2.5 ml of tetrahydrofuran at –40° C. The reaction mixture is allowed to warm up to 0° C. then, at –40° C., 0.09 g of 2-methoxy-4-(4-N-tert-butylcarbamoyl)benzenesulfonyl chloride is added, and it is stirred at 10° C. for 1 hour. 2 ml of water are then added, the mixture is extracted with ethyl acetate, the solvents are evaporated off and the residue is purified on a silica gel column while eluting with a 99/1 dichloromethane/methanol (v/v) mixture to isolate the expected product in the form of a base. 2.7 ml of a 0.1N hydrochloric acid solution in isopropanol are added, the solvent is eliminated, the residue is concreted in 14 ml of diethyl ether. The expected product is isolated in the form of the hydrochloride after filtering and drying at 60° C. under reduced pressure; M.p.=160° C. (HCl, H$_2$O).

EXAMPLE 31

5-Chloro-1-[4-(N-tert-butylcarbamoyl-2-methoxy)benzenesulfonyl]-3-spiro-[4-(3-benzyloxypropylidene)cyclohexane]indolin-2-one.

(I): $R_1$=5-Cl; $R_2$=H; $R_3$=2-OCH$_3$; W=SO$_2$; $R_4$=4-CONHC(CH$_3$)$_3$;

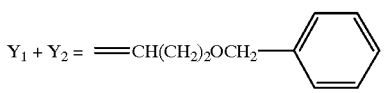

13.8 ml of a 1 M solution of sodium (bistrimethylsilyl)amide in tetrahydrofuran are added to 1.9 g of (3-benzyloxypropyl)triphenylphosphonium bromide in 30 ml of tetrahydrofuran in an inert atmosphere at –10° C. It is stirred for 30 minutes at 20° C. then 1 g of compound (IIA3) in suspension in 40 ml of tetrahydrofuran is added at –70° C. The reaction mixture is stirred for 16 hours, 20 ml of an aqueous 5% ammonium chloride solution are added at 5° C., and it is extracted with ethyl acetate. The organic phase is dried over Na$_2$SO$_4$, the solvents are evaporated off, the residue is chromatographed on a silica gel column while eluting with an 80/20 cyclohexane/ethyl acetate (v/v) mixture, and the expected product is crystallized from isopropyl ether; M.p.=138° C.

EXAMPLE 32

5-Chloro-1-[4-(N-tert-butylcarbamoyl-2-methoxy)benzenesulfonyl]-3-spiro-[4-(3-hydroxypropyl)cyclohexane]indolin-2-one.

(I): $R_1$=5-Cl; $R_2$=H; $R_3$=2-OCH$_3$; W=SO$_2$; $R_4$=4-CONHC(CH$_3$)$_3$; $Y_1$=—(CH$_2$)$_3$OH; $Y_2$=H.

0.29 g of the compound of EXAMPLE 31 in 50 ml of ethanol is hydrogenated at 1 MPa at 18° C. for 20 hours in the presence of 0.08 g of 10% palladium on carbon. The catalyst is separated by filtering, the solvent is evaporated off and the residue is chromatographed on a silica gel column while eluting with an 80/20 cyclohexane/ethyl acetate (v/v) mixture. The expected product is concreted in pentane; M.p.=96° C. (1 cyclohexane).

EXAMPLE 33

1-[(4-N-tert-butylcarbamoyl-2-methoxy)benzenesulfonyl]-3-spiro-[4-(3-hydroxypropyl)cyclohexane]indolin-2-one.

(I): $R_1$=H; $R_2$=H; $R_3$=2-OCH$_3$; W=SO$_2$; $R_4$=4-CONHC(CH$_3$)$_3$; $Y_1$=—(CH$_2$)$_3$OH; $Y_2$=H.

0.25 g of the compound of EXAMPLE 31 in 40 ml of ethanol is hydrogenated at 1.5 MPa at 25° C. for 48 hours in the presence of 0.2 g of 10% palladium on carbon. The catalyst is separated by filtering, the solvent is evaporated off and the residue is chromatographed on a silica gel column while eluting with an 80/20 cyclohexane/ethyl acetate (v/v) mixture. The expected product is concreted in pentane; M.p.=133° C. (0.5 H$_2$0).

EXAMPLE 34

1-[(4-N-tert-butylcarbamoyl-2-methoxy)benzenesulfonyl]-3-spiro-[4-(3-morpholinopropyl)cyclohexane]indolin-2-one.

(I): $R_1$=H; $R_2$=H; $R_3$=2-OCH$_3$; W=SO$_2$; $R_4$=4-CONHC(CH$_3$)$_3$;

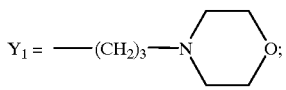

$Y_2$=H.

a) 1-[(4-N-tert-butylcarbamoyl-2-methoxy)benzenesulfonyl]-3-spiro-[4-(3-tosyloxypropyl)cyclohexane]indolin-2-one.

At −10° C., 0.03 g of tosyl chloride is added to 0.06 g of the compound of EXAMPLE 33 in 0.5 ml of pyridine. The reaction mixture is stirred at 0° C. for 3 hours, 5 ml of water are added and then it is extracted with ethyl acetate. The organic phase is dried over Na$_2$SO$_4$, evaporated under reduced pressure, and chromatographed on a silica gel column while eluting with an 85/15 cyclohexane/ethyl acetate (v/v) mixture to isolate the expected product; M.p.= 79° C.

b) 0.02 g of morpholine and 0.01 g of sodium iodide are added to 0.04 g of the above compound in solution in 0.5 ml of dimethylformamide and 1 ml of acetonitrile. The reaction mixture is heated to 75° C. for 16 hours. At 10° C., 5 ml of water are added, the reaction mixture is extracted with ethyl acetate, the solvents are evaporated off, then chromatography is carried out on a silica gel column while eluting with a 98/2 dichloromethane/ethanol (v/v) mixture. It is treated with a solution of HCl in diethyl ether, filtered and dried at 50° C. under reduced pressure to isolate the compound in the form of the hydrochloride; M.p.=157°0 C. (1HCl, 1H$_2$O).

EXAMPLE 35

5-Chloro-1-[(4-N-tert-butylcarbamoyl-2-methoxy)benzenesulfonyl]-3-spiro-4-spiro-(5-dihydro-3H-furan-2-one)cyclohexane]indolin-2-one.

(I): $R_1$=5-Cl; $R_2$=H; $R_3$=2-OCH$_3$; W=SO$_2$; $R_4$=4-CONHC(CH$_3$;

0.04 ml of potassium tert-butoxide is added to a solution of 0.10 g of compound (I'4) and 0.11 g of (2-methoxy-4-N-tert-butylcarbamoyl) benzenesulfonyl chloride in 2.5 ml of tetrahydrofuran at −40° C. The reaction mixture is stirred at 20° C. for 2 hours, 5 ml of water are added and it is then extracted with ethyl acetate. The organic phase is dried over sodium sulfate, the solvents are evaporated off and chroma-tography is carried out on a silica gel column while eluting with a 20/80 cyclohexane/dichloromethane (v/v) mixture. Recrystallization is carried out from a 70/30 cyclohexane/ethyl acetate (v/v) mixture, then filtering and drying at 50° C. under reduced pressure to isolate the expected product; M.p.=268° C.

EXAMPLE 36

5-Chloro-1-[4-(N-tert-butylcarbamoyl-2-methoxy)benzenesulfonyl]-3-spiro-{[4-hydroxy-4-(2-N-(2-carboxamidoethyl)carbamoyl)ethyl]cyclohexane}indolin-2-one.

(I): $R_1$=5-Cl; $R_2$=H; $R_3$=2-OCH$_3$; W=SO$_2$; $R_4$=4-CONHC(CH$_3$)$_3$; $Y_1$=(CH$_2$)$_2$CONH(CH$_2$)$_2$CONH$_2$; $Y_2$=OH.

0.02 g of potassium tert-butoxide is added to a solution of 0.06 g of compound (I'5) in 3 ml of tetrahydrofuran and 1 ml of dimethylformamide. The temperature of the reaction mixture is allowed to rise to 0° C. then, at −60° C., 0.04 g of (2-methoxy-4-N-tert-butylcarbamoyl) benzenesulfonyl chloride in 1.5 ml of tetrahydrofuran is added. At 20° C., 10 ml of water are added, the reaction mixture is extracted with ethyl acetate, the organic phase is dried over Na$_2$SO$_4$, the solvent is evaporated off and chromatography is carried out on a silica gel column while eluting with a 98/2 dichloromethane/methanol (v/v) mixture. The solid obtained is taken up into a hot cyclohexane/ethyl acetate mixture, filtered at 15° C. and dried under reduced pressure. The expected product is thus isolated; M.p.=129° C. (2H$_2$O).

EXAMPLE 37

5-Chloro-1-[4-(N-tert-butylcarbamoyl-2-methoxy)benzenesulfonyl]-3-spiro-[4-(2-tert-butoxycarbonylaminoethyl)cyclohexane]indolin-2-one. (Least polar isomer)

(I): $R_1$=5-Cl; $R_2$=H; $R_3$=2-OCH$_3$; W=SO$_2$; $R_4$=4-CONHC(CH$_3$)$_3$; $Y_1$=—(CH$_2$)$_2$NHCOOC(CH$_3$)$_3$; $Y_2$=H.

0.03 g of potassium tert-butoxide is added to 0.10 g of compound (I'6) in 2.5 ml of tetrahydrofuran and 0.08 g of (2-methoxy-4-N-tert-butylcarbamoyl) benzenesulfonyl chloride at −40° C. The reaction mixture is stirred at 20° C. for 2 hours then 5 ml of water are added and it is extracted with ethyl acetate. It is dried over sodium sulfate, and the solvents are evaporated off. The expected product is isolated by silica gel column chromatography while eluting with a 90/10 cyclohexane/ethyl acetate (v/v) mixture; M.p.=102° C.

EXAMPLE 38

5-Chloro-1-[4-(N-tert-butylcarbamoyl-2-methoxy)benzenesulfonyl]-[3-spiro-4-(2-tert-butoxycarbonylaminoethyl)cyclohexane]indolin-2-one. (Most polar isomer)

(I): $R_1$=5-OC$_2$H$_5$; $R_2$=H; $R_3$=2-OCH$_3$; W=SO$_2$; $R_4$=4-CONHC(CH$_3$)$_3$; $Y_1$=—(CH$_2$)$_2$NHCOOC(CH$_3$)$_3$; $Y_2$=H.

Prepared as described in EXAMPLE 37 from compound (I'7); M.p.=107° C. (1 cyclohexane).

EXAMPLE 39

5-Chloro-3-spiro-[4-(2-aminoethyl)cyclohexane]-1-[4-N-tertbutylcarbamoyl) benzenesulfonyl]indolin-2-one (Most polar isomer).

(I): $R_1$=5-Cl; $R_2$=H; $R_3$=2-OCH$_3$; W=SO$_2$; $R_4$=4-CONHC(CH$_3$)$_3$; $Y_1$=—(CH$_2$)$_2$NH$_2$; $Y_2$=H.

0.25 ml of a saturated solution of hydrogen chloride in ethyl acetate at 15° C. is added, at 0° C. under an inert atmosphere, to 0.025 g of the compound of EXAMPLE 37. The reaction mixture is stirred at 20° C. for 3 hours, the solvent is evaporated off under reduced pressure and the residue is taken up in diethyl ether. The expected product is obtained after filtering and drying at 50° C. under reduced pressure for 5 hours; M.p.=169° C. (HCl, H$_2$O).

EXAMPLE 40

5-Chloro-3-spiro-[4-(2-aminoethyl)cyclohexane]-1-[4-N-tertbutylcarbamoyl)benzenesulfonyl]indolin-2-one (Least polar isomer).

(I): R$_1$=5-Cl; R$_2$=H; R$_3$=2-OCH$_3$; W=SO2; R$_4$=4-CONHC(CH$_3$)$_3$; Y$_1$=—(CH$_2$)$_2$NH$_2$; Y$_2$=H.

Prepared from the compound of EXAMPLE 38 using the same operating procedure as that described in EXAMPLE 39; M.p.=193° C. (HCl).

EXAMPLE 41

5-Chloro-3-spiro-[4-(2-(2-carboxamidoethyl) carbonylaminoethyl)cyclo-hexane]-1-[(4-N-tert-butylcarbamoyl-2-methoxy)benzenesulfonyl]indolin-2-one.

(I): R$_1$=5-Cl; R$_2$=H; R$_3$=2-OCH$_3$; W=SO$_2$; R$_4$=CONHC(CH$_3$)$_3$; Y$_1$=—(CH$_2$)$_2$NHCO(CH$_2$)$_2$CONH$_2$; Y$_2$=H.

0.007 g of succinamic acid, 0.026 g of benzotriaz-1-yl oxy-tris-(dimethylamino)-phosphonium hexafluorophosphate and 0.02 ml of triethylamine are added to 0.029 g of the compound of EXAMPLE 39 in 1.5 ml of acetonitrile. The reaction mixture is stirred at 20° C. for 3 hours, the solvent is evaporated off under reduced pressure, the residue is taken up in 2 ml of 5% NaHCO$_3$ and extracted with ethyl acetate. The organic phase is dried over sodium sulfate, and the solvent is evaporated off. The residue obtained is purified on a silica gel chromatographic column while eluting with dichloromethane then concreted in pentane and dried at 50° C. under reduced pressure. 10 The expected product is isolated; M.p.=128° C.

EXAMPLE 42

5-Chloro-1-[(2-methoxy-4-tert-butylcarbamoyl) benzenesulfonyl]-3-spiro-[4-tert-butoxycarbonylaminomethyl)cyclohexane]indolin-2-one.

(I): R$_1$=5-Cl; R$_2$=H; R$_3$=2-OCH$_3$; W=SO$_2$; R$_4$=CONHC(CH$_3$)$_3$; Y$_1$=(CH$_2$)NHCOOC(CH$_3$)$_3$; Y$_2$=H.

0.03 g of potassium tert-butoxide is added to a solution of 0.09 g of compound (I'8) and 0.08 g of (4-tert-butylcarbamoyl-2-methoxy) benzenesulfonyl chloride in 2.5 ml of tetrahydrofuran at −50° C. At 20° C., 4 ml of water are added, the reaction mixture is extracted with ethyl acetate, dried over sodium sulfate, and the solvents are evaporated off under reduced pressure. The expected product (mixture of isomers) is isolated after chromatography on a silica gel column while eluting with dichloromethane; M.p.=95° C.

EXAMPLE 43

5-Chloro-3-spiro-(4-tert-butoxycarbonylaminomethylcyclohexane)-1-[(2,4-dimethoxy)benzenesulfonyl]indolin-2-one.

(I): R$_1$=5-Cl; R$_2$=H; R$_3$=2-OCH$_3$; W=SO$_2$; R$_4$=4-OCH$_3$; Y=(CH$_2$)NHCOOC(CH$_3$)$_3$; Y$_2$=H.

Prepared using the operating procedure as that described in EXAMPLE 42, starting from (2,4-dimethoxy) benzenesulfonyl chloride.

$^1$H NMR: 7.9 (m, 1H); 7.6 (m, 2H); 7.4 (m, 0.3H); 7.3 (m, 0.7H); 6.8–6.6 (m, 2H); 3.8 (s, 3H); 3.5 (s, 3H); 3.0 (m, 0.6H); 2.8 (m, 1.4H); 1.9–1.4 (m, 9H); 1.4 (s, 6.3H); 1.3 (s, 2.7H)

EXAMPLE 44

5-Chloro-3-spiro-(4-aminomethylcyclohexane)-1-[(2,4-dimethoxy)benzenesulfonyl]indolin-2-one.

(I): R$_1$=5-Cl; R$_2$=H; R$_3$=2-OCH$_3$; W=SO$_2$; R$_4$=2-OCH$_3$; Y$_1$=(CH$_2$)NH$_2$; Y$_2$=H.

Prepared from the compound of EXAMPLE 43 using the operating procedure described in EXAMPLE 39; M.p.=195° C. (HCl).

What is claimed is:

1. Compounds with formula:

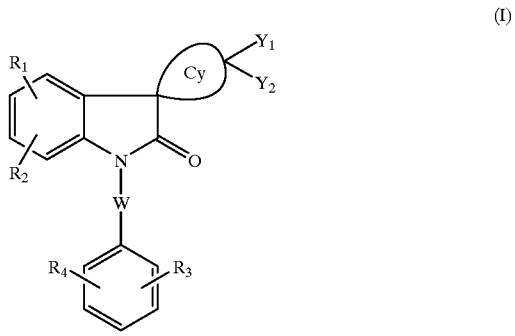

where:

R$_1$ and R$_2$ each independently represent a hydrogen; a hydroxyl; a halogen; a (C$_1$–C$_7$)alkyl; a (C$_1$–C$_7$) polyfluoroalkyl; a (C$_1$–C$_7$)alkoxy; a (C$_1$–C$_7$)alkylthio; a (C$_1$–C$_7$)polyfluoroalkoxy; a (C$_3$–C$_7$)cycloalkyloxy; a (C$_3$–C$_7$)cycloalkylthio; a cycloalkylmethoxy or a cycloalkylmethylthio in which the cycloalkyl is C$_3$–C$_7$; a phenoxy; a benzyloxy; a nitro; a cyano;

R$_3$ and R$_4$, independently of each other, substitute the phenyl group one or more times and each independently represent hydrogen; a halogen; a (C$_1$–C$_7$)alkyl; a (C$_2$–C$_7$)alkenyl; a (C$_1$–C$_7$)polyhalogenoalkyl; a phenyl or a benzyl; a cyano; a nitro; a —NR$_5$R$_6$ group; a hydroxyamino; a hydroxyl; a OR$_7$ group; a SR$_7$ group; a —COOR$_8$ group; a —CONR$_9$R$_{10}$ group; a —CSNR$_9$R$_{10}$ group, at least one of radicals R$_3$ and R$_4$ being other than hydrogen;

R$_5$ and R$_6$ each independently represent hydrogen; a (C$_1$–C$_7$)alkyl; a (C$_2$–C$_7$)alkenyl; a phenyl; a benzyl; a (C$_1$–C$_7$)alkylcarbonyl; a (C$_1$–C$_7$)alkylthlocarbonyl; a (C$_3$–C$_7$)cycloalkylcarbonyl; a (C$_3$–C$_7$)cycloalkylthiocarbonyl; a benzoyl; a thienylcarbonyl; a furylcarbonyl; a (C$_1$–C$_7$)alkyloxycarbonyl; a phenoxycarbonyl; a benzyloxycarbonyl; a carbamoyl or a thiocarbamoyl not substituted or substituted by R$_9$ and R$_{10}$, or R$_5$ and R$_6$ together with the nitrogen to which they are bonded constitute a heterocyclic group selected from pyrrolidine, pyrroline, pyrrole, indoline, indole, piperidine groups; or R$_5$ together with the nitrogen atom to which it is bonded and the carbon atom adjacent to the phenyl group constitutes a heterocycle selected from indole, indoline and tetrahydroquinoline, and R$_6$ represents hydrogen; a (C$_1$–C$_7$)alkyl; a benzyl; a (C$_1$–C$_7$)alkylcarbonyl; a (C$_1$–C$_7$)alkylthlocarbonyl; a (C$_3$–C$_7$) cycloalkylcarbonyl; (a C$_3$–C$_7$)cycloalkylthiocarbonyl; a (C$_1$–C$_7$)alkyloxycarbonyl; a phenoxycarbonyl; a benzyloxycarbonyl; a carbamoyl or a thiocarbamoyl group not substituted or substituted by R$_9$ and R$_{10}$;

R$_7$ represents a (C$_1$–C$_7$)alkyl; a (C$_2$–C$_7$)alkenyl; a phenyl; a benzyl; a (C$_3$–C$_7$)cycloalkyl; a (C$_1$–C$_7$)

polyfluoroalkyl; a formyl; a (C₁–C₇) alkylcarbonyl; a benzoyl; a benzylcarbonyl;

R₈ represents hydrogen; a (C₁–C₇)alkyl; a phenyl; a benzyl;

R₉ and R₁₀ each independently represent hydrogen; a (C₁–C₇)alkyl; a (C₁–C₇)polyfluoroalkyl; a (C₂–C₇) alkenyl; a (C₃–C₇)cycloalkyl optionally substituted by a hydroxy(C₁–C₄)alkyl group; a pyridyl; a phenyl; a thienyl; a furyl; or R₉ and R₁₀ together with the nitrogen atom to which they are bonded constitute a heterocyclic group selected from pyrrolidine, piperidine or piperazine groups not substituted or substituted by one or more (C₁–C₄)alkyl group(s); and the (C₆–C₇) azacycloalkyl group;

W represents a —CH₂— or —SO₂— group;

Cy constitutes, together with the carbon atom to which it is bonded, a non aromatic, saturated or unsaturated C₅–C₁₂ hydrocarbon cycle, optionally condensed or substituted by one or more (C₁–C₇)alkyl group(s), said groups possibly substituting the same carbon atom one or more times, or by a C₃–C₆ spirocycloalkyl group;

Y₁ and Y₂ substitute the same carbon atom of Cy, and

Y₁ represents either
   (i) a (C₀–C₄)alkylene-T—Z group,
   (ii) a (C₀–C₃)alkylene —NR₁₆—T—Z group in which R₁₆ represents a hydrogen atom, a (C₁–C₃)alkyl, an oxygen atom, the nitrogen atom carrying the R₁₆ optionally being quaternary, with the counter-anion then being Cl⁻, Br⁻, I⁻ or CH₃SO⁻₄;
   (iii) a (C₁–C₃)alkylene-O—T—Z group
   (iv) a (C₀–C₃)alkylene-S—T—Z group
       a (C₀–C₃)alkylene-SO—T—Z group
       a (C₀–C₃)alkylene-SO₂—T—Z group Y₂ represents a hydrogen atom or a hydroxyl group or forms with Y₁ a (C₁–C₄)alkylidene-T—Z group, a (C₂–C₃)alkylidene —NR₁₆—T—Z group in which R₁₆ is as defined above or (C₂–C₃)alkylidene-O—T—Z furan-2-one;

T represents a (C₁–C₄)alkylene optionally interrupted by a (C₃–C₆)cycloalkylene, said alkylenes optionally being substituted one or more times on the same carbon atom by a (C₁–C₃)alkyl group; or T represents a direct bond;

Z represents hydroxyl; a benzyloxy; a —NR₁₁R₁₂ group; a —⁺NR₁₁R₁₂ (C₁–C₄)alkyl (A⁻), (A⁻) being Cl⁻, Br⁻, I⁻ or CH₃SO₄⁻; a —N(O)R₁₁R₁₂; a —COOR₁₁ group; a —NR₁₁COR₁₂ group; a benzyloxycarbonylamino; or a —CONR₁₁R₁₂ group, it being understood that:
   when Y₁ is as defined in cases (ii), (iii) and (iv) and when T represents a methylene group or a direct bond, Z cannot be a hydroxyl; a benzyloxy; a —NR₁₁R₁₂; a N(O)R₁₁R₁₂; a —⁺NR₁₁R₁₂(C₁–C₄) alkyl; a —NR₁₁COR₁₂; or a benzyloxycarbonylamino,
   or when Y₁=Z, Z cannot be a hydroxyl or a benzyloxy;

R₁₁ and R₁₂ each independently represent hydrogen; a (C₁–C₇)alkyl; a (C₁–C₄)alkoxy; a (C₃–C₇)cycloalkyl; a phenyl; a (C₁–C₃) alkylene which is substituted by a (C₃–C₇) group or by a phenyl, where the cycloalkyl is C₃–C₇, a (C₁–C₃) alkylenephenyl, said groups optionally being mono or polysubstituted by R₁₃;wherein the phenyl group constitutive of R₁, R₂, R₃, R₄, R₅, R₆, R₇, R₈, R₉, R₁₀, R₁₁, and R₁₂, can be non substituted, mono- or di-substituted by a (C₁–C₇) alkyl, a trifluoromethyl, a (C₁–C₇) alkoxy, a halogen or trisubstituted by a (C₁–C₇) alkyl, a (C₁–C₇) alkoxy or a halogen, or R₁₁ and R₁₂, together with the nitrogen atom to which they are bonded, optionally constitute a heterocycle selected from the heterocycles: azetidine, pyrrolidine, piperidine, piperazine, piperazinone, morpholine, morpholinone, thiomorpholine, hexahydroazepine optionally mono- or poly-substituted by R₁₃; or a thiomorpholine-1,1-dioxide or a thiomorpholine-1-oxide; or R₁₂ represents pyrrolidone or piperidone;

R₁₃ represents a hydroxyl group; a (C₁–C₄)alkyl; a (C₁–C₄)alkoxy; a mercapto; a (C₁–C₄)alkylthio; a (C₁–C₄)alkylsulfinyl; a (C₁–C₄)alkylsulfonyl; a benzyloxy or hydroxyalkyloxy; a NR₁₄R₁₅ group where R₁₄ and R₁₅ each independently represent hydrogen or a (C₁–C₄)alkyl or a (C₁–C₄)alkyloxycarbonyl or a benzyloxycarbonyl; a carboxy; a (C₁–C₄) alkyloxycarbonyl, a phenoxycarbonyl; a benzyloxycarbonyl; a carbamoyl; an amidino; a guanidino; an imidazolyl; a thienyl; a pyridyl; an indolyl; a tetrahydroisoquinolyl;

and their salts, solvates or hydrates.

2. Compounds according to claim 1 with formula:

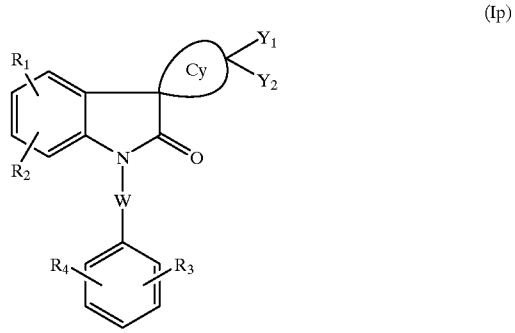

(Ip)

where:
R₁ and R₂ each independently represent a hydrogen; a hydroxyl; a halogen; a (C₁–C₇)alkyl; a (C₁–C₇) polyfluoroalkyl; a (C₁–C₇)alkoxy; a (C₁–C₇)alkylthio; a (C₁–C₇)polyfluoroalkoxy; a (C₃–C₇)cycloalkyloxy; a (C₃–C₇) cycloalkylthio; a cycloalkylmethoxy or a cycloalkylmethylthio in which the cycloalkyl is C₃–C₇; a phenoxy; a benzyloxy; a nitro; a cyano;

R₃ and R₄ independently of each other substitute the phenyl group one or more times and each independently represent hydrogen; a halogen; a (C₁–C₇)alkyl; a (C₂–C₇)alkenyl; a (C₁–C₇)polyhalogenoalkyl; a phenyl or a benzyl; a cyano; a nitro; a —NR₅R₆ group; a hydroxyamino; a hydroxyl; an OR₇ group; a SR₇ group; a —COOR₈ group; a —CONR₉R₁₀ group; a —CSNR₉R₁₀ group, at least one of radicals R₃ and R₄ being other than hydrogen;

R₅ and R₆ each independently represent a hydrogen; a (C₁–C₇)alkyl; a (C₂–C₇)alkenyl; a phenyl; a benzyl; a (C₁–C₇)alkylcarbonyl; a (C₁–C₇)alkylthiocarbonyl; a (C₃–C₇)cycloalkylcarbonyl; a (C₃–C₇) cycloalkylthiocarbonyl; a benzoyl; a thienylcarbonyl; a furylcarbonyl; a (C₁–C₇) alkyloxycarbonyl; a phenoxycarbonyl; a benzyloxycarbonyl; a carbamoyl or a thiocarbamoyl substituted or not substituted by R₉ and R₁₀, or R₅ and R₆ together with the nitrogen atom to which they are bonded constitute a heterocyclic group selected from the groups: pyrrolidine, pyrroline, pyrrole, indoline, indole, piperidine; or $R_5$ together with the nitrogen atom to which it is bonded and the carbon atom adjacent to the phenyl group constitute a heterocycle selected from indole, indoline and tetrahydroquinoline and $R_6$ represents hydrogen; a $(C_1-C_7)$alkyl; a benzyl; a $(C_1-C_7)$alkylcarbonyl; a $(C_1-C_7)$alkylthiocarbonyl; a $(C_3-C_7)$cycloalkylcarbonyl; a $(C_3-C_7)$cycloalkylthiocarbonyl; a $(C_1-C_7)$alkyloxycarbonyl; a phenoxycarbonyl; a benzyloxycarbonyl; a carbamoyl or a thiocarbamoyl group not substituted or substituted by $R_9$ and $R_{10}$;

$R_7$ represents a $(C_1-C_7)$alkyl; a $(C_2-C_7)$alkenyl; a phenyl; a benzyl; a $(C_3-C_7)$cycloalkyl; a $(C_1-C_7)$polyfluoroalkyl; a formyl; a $(C_1-C_7)$ alkylcarbonyl; a benzoyl; a benzylcarbonyl;

$R_8$ represents hydrogen, a $(C_1-C_7)$alkyl; a phenyl; a benzyl;

$R_9$ and $R_{10}$ each independently represent hydrogen; a $(C_1-C_7)$alkyl; a $(C_1-C_7)$polyfluoroalkyl; a $(C_2-C_7)$alkenyl; a $(C_3-C_7)$cycloalkyl optionally substituted by a hydroxy$(C_1-C_4)$alkyl group; a pyridyl; a phenyl; a thienyl; a furyl; or $R_9$ and $R_{10}$ together with the nitrogen atom to which they are bonded constitute a heterocyclic group selected from the groups: pyrrolidine, piperidine or piperazine substituted or not substituted by $(C_1-C_4)$alkyl groups; and the $(C_6-C_7)$ azacycloalkyl group; group W represents a —$CH_2$— or —$SO_2$— group;

Cy, together with the carbon atom to which it is bonded, constitutes a non aromatic, saturated or unsaturated $C_5-C_{12}$ group, optionally condensed or substituted by one or more $(C_1-C_7)$alkyl groups, said groups possibly being substituted one or more times on the same carbon atom or by a $C_3-C_6$ spirocycloalkyl group;

$Y_1$ and $Y_2$ substitute the same carbon atom of Cy and $Y_1$ represents either
 (i) a $(C_0-C_4)$alkylene-T—Z group, a $(C_1-C_4)$ alkylidene-T—Z group,
 (ii) a $(C_0-C_3)$alkylene —$NR_{16}$—T—Z group where $R_{16}$ represents a hydrogen atom, a $(C_1-C_3)$alkyl, an oxygen atom, the nitrogen atom carrying the $R_{16}$ optionally being quaternary, the counter-anion then being as defined in Z,
 (iii) a $(C_1-C_3)$alkylene-O—T—Z group $Y_2$ represents a hydrogen atom or a hydroxyl group or forms with $Y_1$ a $(C_1-C_4)$alkylidene-T—Z group, a $(C_2-C_3)$alkylidene —$NR_{16}$—T—Z group in which $R_{16}$ is as defined above or a $(C_2-C_3)$alkylidene-O—T—Z group;

T represents a $(C_1-C_4)$alkylene group optionally interrupted by a $(C_3-C_6)$cycloalkylene group, said alkylenes optionally being substituted one or more times on the same carbon atom by a $(C_1-C_3)$alkyl; or T represents a direct bond;

Z represents a —$NR_{11}R_{12}$ group; a —$^+NR_{11}R_{12}(C_1-C_4)$ alkyl $(A^-)$, $(A^-)$ being $Cl^-$, $Br^-$, $I^-$ or $CH_3SO_4^-$; a —$N(O)R_{11}R_{12}$; a —$COOR_{11}$ group; a —$NR_{11}COR_{12}$ group; a benzyloxycarbonylamino; a —$CONR_{11}R_{12}$ group, it being understood that when $Y_1$ is as defined in case (ii) and (iii) and when T represents a methylene group or a direct bond, then Z cannot be —$NR_{11}R_{12}$; —$^+NR_{11}R_{12}$; $(C_1-C_4)$alkyl; —$NR_{11}COR_{12}$; or a benzyloxycarbonylamino group;

$R_{11}$ and $R_{12}$ each independently represent hydrogen; a $(C_1-C_7)$alkyl; a $(C_1-C_7)$alkoxy; a $(C_3-C_7)$cycloalkyl; a phenyl; said groups optionally being mono or polysubstituted by $R_{13}$; or $R_{11}$ and $R_{12}$ together with the nitrogen atom to which they are bonded optionally constitute a heterocycle selected from the heterocycles: azetidine, pyrrolidine, piperidine, piperazine, piperazinone, morpholine, morpholinone, thiomorpholine, hexahydroazepine optionally mono or polysubstituted by $R_{13}$; a $(C_1-C_3)$alkylene substituted by a $(C_3-C_7)$ cycloalkyl group or by a phenyl, or a thiomorpholine-1,1-dioxide or a thiomorpholine-1-oxide; or $R_{12}$ represents a pyrrolidone or a piperidone;

$R_{13}$ represents a hydroxyl group; a $(C_1-C_4)$alkyl; a $(C_1-C_4)$alkoxy; a mercapto; a $(C_1-C_4)$alkylthio; a $(C_1-C_4)$alkylsulfinyl; a $(C_1-C_4)$alkylsulfonyl; a benzyloxy or a hydroxyalkyloxy; a $NR_{14}R_{15}$ group where $R_{14}$ and $R_{15}$ each independently represent hydrogen or a $(C_1-C_4)$alkyl or a $(C_1-C_4)$alkyloxycarbonyl or a benzyloxycarbonyl; a carboxyl group; a $(C_1-C_4)$ alkyloxycarbonyl, a phenoxycarbonyl; a benzyloxycarbonyl; a carbamoyl; an amidino; a guanidino; an imidazolyl; a thienyl; a pyridyl; an indolyl; a tetrahydroisoquinolyl;

and their salts, solvates or hydrates.

3. Compounds according to claim 1 with formula (IA):

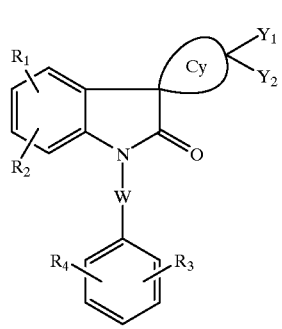

(IA)

where substituent $R_1$ is in the 5 position of the indolin-2-one, $R_2$ represents hydrogen and Cy, $Y_1$, $Y_2$, $R_3$, $R_4$ and W are as defined for I and their salts, hydrates or solvates.

4. A compound according to claim 3, wherein Cy represents a cyclohexyl, $Y_1$ and $Y_2$ substitute the 4 position of the cyclohexyl; $R_1$ represents a chlorine atom; W represents $SO_2$; and salt, hydrates and solvates thereof.

5. A compound according to claim 3, wherein Cy represents a cyclohexyl, $Y_1$ and $Y_2$ substitute the 4 position of the cyclohexyl; $R_1$ represents an ethoxy; W represents $SO_2$; and salts, hydrates and solvates thereof.

6. A pharmaceutical composition comprising, as an active principle, a compound with formula (I) according to claim 1, or a pharmaceutically acceptable salt, hydrate or solvate thereof.

7. A pharmaceutical composition comprising, as an active principle, a compound with formula (I) according to claim 2, or a pharmaceutically acceptable salt, hydrate or solvate thereof.

8. A pharmaceutical composition comprising, as an active principle, a compound with formula (I) according to claim 3, or a pharmaceutically acceptable salt, hydrate or solvate thereof.

9. A pharmaceutical composition comprising, as an active principle, a compound with formula (I) according to claim 4, or a pharmaceutically acceptable salt, hydrate or solvate thereof.

10. A pharmaceutical composition comprising, as an active principle, a compound with formula (I) according to claim 5, or a pharmaceutically acceptable salt, hydrate or solvate thereof.

11. A pharmaceutical composition according to claim 7, further comprising a second active principle.

12. A pharmaceutical composition according to claim 11, wherein the second active principle is a specific antagonist for the angiotensin II receptor.

13. A pharmaceutical composition according to claim 12, wherein the specific antagonist for the angiotensin II receptor is irbesartan.

14. A process for the preparation of a compound of formula (I), according to claim 1, comprising:

reacting a compound of formula (I'):

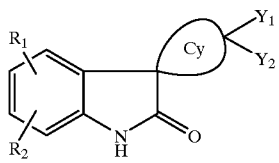

wherein $R_1$, $R_2$, Cy, $Y_1$ and $Y_2$ are defined according to claim 1, with a compound of formula (2):

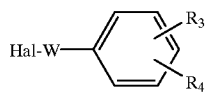

(2)

wherein W, $R_3$ and $R_4$ are defined according to claim 1 and Hal represents a halogen atom,
in the presence of a metallic hydride or an alkaline alcoholate at a temperature of between minus 40° C. and 25° C., in an anhydrous solvent.

15. A method of treating or preventing a condition associated with vasopressin or oxytocin activity comprising administering to a patient in need of such treatment a therapeutically effective amount of a compound of formula (I), according to claim 1, or a pharmaceutically acceptable salt, solvate or hydrate thereof.

16. A method according to claim 15, wherein the condition associated with vasopressin or oxytocin activity is selected from disorders of the central and peripheral nervous system, the cardiovascular system, the endocrine and hepatic system, the renal sphere, the gastric, intestinal and pulmonary sphere and the optic system.

17. A method according to claim 16, wherein the conditions associated with vasopressin or oxytocin activity is selected from hypertension, pulmonary hypertension, cardiac insufficiency, circulatory insufficiency, myocardial infarctus, atherosclerosis, coronary vasospasm, unstable angina, percutaneous transluminal coronary angioplasty, cardiac ischemia, disorders in haemostasis, haemophilia, Von Willebrand's syndrome, disorders of the central nervous system, migraine, cerebral vasospasm, cerebral hemorraghia, cerebral oedemas, depression, anxiety, bulimia, psychotic states, renopathies, oedemas, renal vasospasm, necrosis of the renal cortex, nephrotic syndrome, hyponatremia, hypokalemia, diabetes, Schwartz-Bartter syndrome or renal lithiasis, gastric vasospasm, portal hypertension, hepatocirrhosis, ulcers, vomiting, cirrhosis of the liver, abdominal ascitis, abnormal water retention, Cushing's disease, hypercorticism and hyperaldosteronemia, pancreatic disorders, the regulation of lipid metabolism, sexual behavioral disorders, obesity, dysmenorrhea, premature labor, small cell pulmonary cancer, hyponatremic encephalopathy, Raynaud's disease, Meniere's syndrome, pulmonary syndrome, glaucoma and cataracts.

18. A method of inhibiting vasopressin or oxytocin activity in a patient, comprising administering to the patient a therapeutically effective amount of a compound of formula (I), according to claim 1, or a pharmaceutically acceptable salt thereof.

* * * * *